United States Patent
Sergeeva et al.

(10) Patent No.: US 11,712,444 B2
(45) Date of Patent: Aug. 1, 2023

(54) COMPOSITIONS AND METHODS OF TREATING NEURONAL INJURY

(71) Applicants: CHILDREN'S MEDICAL CENTER CORPORATION, Boston, MA (US); GEORGIA TECH RESEARCH CORPORATION, Atlanta, GA (US)

(72) Inventors: Elena G. Sergeeva, Boston, MA (US); Paul A. Rosenberg, Boston, MA (US); Larry I. Benowitz, Boston, MA (US); Christoph J. Fahrni, Atlanta, GA (US); Michael Thomas Morgan, Atlanta, GA (US)

(73) Assignees: CHILDREN'S MEDICAL CENTER CORPORATION, Boston, MA (US); GEORGIA TECH RESEARCH CORPORATION, Atlanta, GA (US)

( * ) Notice: Subject to any disclaimer, the term of this patent is extended or adjusted under 35 U.S.C. 154(b) by 136 days.

(21) Appl. No.: 17/015,625

(22) Filed: Sep. 9, 2020

(65) Prior Publication Data
US 2021/0069216 A1   Mar. 11, 2021

Related U.S. Application Data

(60) Provisional application No. 62/897,694, filed on Sep. 9, 2019.

(51) Int. Cl.
| | | |
|---|---|---|
| A61K 31/66 | (2006.01) | |
| A61P 25/00 | (2006.01) | |
| A61K 9/00 | (2006.01) | |

(52) U.S. Cl.
CPC ............ *A61K 31/66* (2013.01); *A61K 9/0048* (2013.01); *A61K 9/0085* (2013.01); *A61P 25/00* (2018.01)

(58) Field of Classification Search
CPC .... A61K 31/66; A61K 9/0048; A61K 9/0085; A61P 25/00
USPC ....................................................... 514/107
See application file for complete search history.

(56) References Cited

PUBLICATIONS

Morgan et al., "Ratiometric two-photon microscopy reveals attomolar copper buffering in normal and Menkes mutant cells," Proceedings of the National Academy of Sciences of the United States, Jun. 18, 2019, vol. 116, No. 25, pp. 12167-12172.
Morgan et al., "Stabilization of Aliphatic Phosphines by Auxiliary Phosphine Sulfides Offers Zeptomolar Affinity and Unprecedented Selectivity for Probing Biological Cu(I)," Angewandte Chemie International Edition, Jul. 26, 2018, vol. 57, No. 31, pp. 9711-9715.
Saeedifard et al., "Preorganized PSP Ligands Yield Monomeric Cu(I) Complexes with Sub-zeptomolar Cu(I) Dissociation Constants," Inorganic Chemistry, 2019, vol. 58, No. 20, pp. 13631-13638.

*Primary Examiner* — Kristin A Vajda
(74) *Attorney, Agent, or Firm* — Melissa Hunter-Ensor; Greenberg Traurig, LLP

(57) ABSTRACT

The present invention features methods and composition directed to treating neuronal injury, CNS lesion, and/or promoting axon regeneration using a phosphine sulfide-stabilized phosphine.

3 Claims, 24 Drawing Sheets

COMPOSITIONS AND METHODS OF TREATING NEURONAL INJURY

CROSS-REFERENCE TO RELATED APPLICATIONS

This application is a U.S. Utility Application, filed pursuant to 35 U.S.C. § 111, which claims the benefit of and priority to U.S. Provisional Application No. 62/897,694, filed on Sep. 9, 2019. The entire contents of which is incorporated herein by reference.

STATEMENT OF RIGHTS TO INVENTIONS MADE UNDER FEDERALLY SPONSORED RESEARCH

This invention was made with government support under Grant Nos. 1R01EY027881-01A1 and SR01EY024481-05 awarded by the National Institutes of Health. The government has certain rights in the invention.

BACKGROUND OF THE INVENTION

Traumatic optic nerve injury is one of the complications of head trauma. Such injury may lead to axonal degeneration, followed by a gradual death of retinal ganglion cells (RGCs), which results in irreversible vision loss. Diseases in humans associated with optic nerve injury include traumatic optic neuropathy and optic nerve degeneration in glaucoma. Such diseases are characterized by typical changes in the optic nerve head, progressive optic nerve degeneration, and loss of retinal ganglion cells, which if uncontrolled, may lead to vision loss and blindness. Currently, there is no effective method for promoting the regeneration of neurons within the mammalian central nervous system available. Accordingly, therapeutic approaches for treating optic nerve injury or other CNS lesions are needed.

SUMMARY OF THE INVENTION

As described below, the present invention features methods and composition directed to treating neuronal injury, CNS lesion, and/or promoting axon regeneration using phosphine sulfide-stabilized phosphines, which are high affinity copper chelators (e.g., PSP-1, PSP-2, phenPS, naphPS).

One aspect of the present invention provides a composition for treating a neuronal injury, the composition includes a phosphine sulfide-stabilized phosphine and a pharmaceutically acceptable carrier excipient. In some embodiments, the phosphine sulfide-stabilized phosphine is PSP-1, PSP-2, phenPS, or naphPS. In some embodiments, the phosphine sulfide-stabilized phosphine is PSP-2. In some embodiments, the composition includes an amount of a phosphine sulfide-stabilized phosphine sufficient to increase axon outgrowth subsequent to nerve injury relative to the amount of axon outgrowth detected in a corresponding control cell.

In another aspect, the invention provides a method for promoting axon regeneration, the method involving contacting a neuron at a site of injury with a phosphine sulfide-stabilized phosphine.

Another aspect provides a method of treating a subject having a central nervous system lesion, and the method involves administering to the subject a phosphine sulfide-stabilized phosphine. In some embodiments, the phosphine sulfide-stabilized phosphine is PSP-1, PSP-2, PhenPS, or naphPS. In some embodiments, the phosphine sulfide-stabilized phosphine is PSP-2. In some embodiments, the contacting or administering occurs prior to, during, or subsequent to the injury. In some embodiments, the phosphine sulfide-stabilized phosphine is administered prior to a surgical procedure. In some embodiments, the contacting or administering occurs within about 1, 6, 12, or 24 hours of the injury. In some embodiments, the contacting or administering occurs within about 1-3 days of the injury. In some embodiments, the administering is local or systemic. In some embodiments, the administering is sustained for days, weeks, or months. In some embodiments, the subject is a mammal. In some embodiments, the subject is a human. In some embodiments, the injury or CNS lesion results from an acute traumatic injury. In some embodiments, the acute traumatic injury is selected from the group consisting of stroke, acute spinal cord injury, and traumatic brain injury. In some embodiments, the lesioned CNS neuron is in the optic nerve. In some embodiments, the administering is ocular. In some embodiments, the lesioned CNS neuron is in the spinal cord of a patient, and the inhibitor is intrathecally administered to the patient. In some embodiments, the lesioned CNS neuron is a sensory neuron.

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof. In one embodiment, the agent is a phosphine sulfide-stabilized phosphine (PSP) (e.g., PSP-1, PSP-2, phenPS, and naphPS).

By "ameliorate" is meant decrease, suppress, attenuate, diminish, arrest, or stabilize the development or progression of an injury, disease, or condition. In one embodiment, the invention provides a method for ameliorating the effects of neuronal injury.

By "alteration" is meant a change (increase or decrease) in an analyte as detected by standard art known methods such as those described herein. As used herein, an alteration includes a 10% change, preferably a 25% change, more preferably a 40% change, and most preferably a 50% or greater change. In particular embodiments, an alteration refers to an increase or decrease in axon regeneration. In another embodiment, an alteration refers to an increase or decrease in intracellular Copper levels.

The term "axon growth" "axon outgrowth" refers to the process by which axons extend from a neuron.

"Axon regeneration" refers to axon growth after an injury or damage to a neuron, nerve, or axons which comprise a nerve. Some forms of damage to a neuron, nerve, or axons can be directly detected using well established methods (e.g., by visualization as with a severed or crushed neuronal axon).

By "βIII-tubulin" is meant a cell-specific protein expressed specifically in retinal ganglion cells in the retina.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "chelator" or "chelating agent" is meant a small molecule that binds one or more metals with high affinity. In some embodiments, the chelating agent is a phosphine sulfide-stabilized phosphine (PSP).

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases contemplated herein include any disease that is treated by promoting axonal regeneration. Examples include brain trauma, eye trauma, stroke spinal cord injury, and glaucoma.

By "effective amount" is meant the amount of an agent or compound required to ameliorate the symptoms of an injury, disease, or neurological condition relative to an untreated patient. In one embodiment, an effective amount is the amount of an agent (e.g., a phosphine sulfide-stabilized phosphine) required to promote axonal outgrowth or to otherwise ameliorate the effects of neuronal injury. The effective amount of active compound(s) used to practice the present invention for therapeutic treatment of an injury, disease, or neurological condition varies depending upon the manner of administration, the age, body weight, and general health of the subject. Ultimately, the attending physician or veterinarian will decide the appropriate amount and dosage regimen. Such amount is referred to as an "effective" amount. In one embodiment, an effective amount is the amount needed to promote axonal regeneration.

The methods of the invention provide a facile means to identify therapies that are safe for use in subjects. In addition, the methods of the invention provide a route for analyzing virtually any number of compounds for effects on an injury, disease, or neurological condition described herein with high-volume throughput, high sensitivity, and low complexity.

By "Growth Associated Protein 43" or "GAP-43 protein" is meant a nervous tissue specific protein expressed at high levels during axon growth or regeneration.

By "marker" is meant any protein or polynucleotide having an alteration in expression level or activity that is associated with a disease, injury, or a health status. For example, GAP-43 is a marker of axon growth.

The term "neuronal injury" refers to any damage incurred by a neuron. In one embodiment, neuronal injury results in the death of the neuron. In another embodiment, neuronal injury results in a loss of neuronal function. In some embodiments, neuronal injury results in a CNS lesion.

As used herein, "obtaining" as in "obtaining an agent" includes synthesizing, purchasing, or otherwise acquiring the agent.

As used herein, the terms "prevent," "preventing," "prevention," "prophylactic treatment" and the like refer to reducing the probability of an incurring an injury or developing a disease or neurological condition in a subject, who does not have, but is at risk of or susceptible to an injury or developing disease or neurological condition.

By "reduces" is meant a negative alteration of at least 10%, 25%, 50%, 75%, or 100%.

By "reference" is meant a standard or control condition.

"Selectively binds" refers to an agent that binds a target with high affinity, but does not detectably bind other targets. For example, PSP-1, PSP-2, phenPS, and naphPS are copper chelators that bind Cu(I) with high affinity and do not bind other ions.

By "subject" is meant a mammal, including, but not limited to, a human or non-human mammal, such as a bovine, equine, canine, ovine, or feline.

As used herein, the terms "treat," "treating," "treatment," and the like refer to reducing or ameliorating an injury, disease, or neurological condition and/or symptoms associated therewith. It will be appreciated that, although not precluded, treating an injury, disease, or neurological condition does not require that the injury, disease, or neurological condition or symptoms associated therewith be completely eliminated.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a," "an," and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 3A is a graph showing the estimated number of axons per nerve 0.5 mm from the crush site after treatment of ONC with DMSO, TPEN, PSP-2, and PSP-2+Cu. FIG. 3B is a graph showing the number of axons 1.0 mm from the crush site after treatment of ONC with DMSO, TPEN, PSP-2, and PSP-2+Cu.

FIG. 4A is an image of a longitudinal section of the optic nerve of a mouse treated with DMSO after ONC that shows GAP-43-positive axons. FIG. 4B is an image of a longitudinal section of the optic nerve of mouse #3 that shows GAP-43-positive axons. FIG. 4C is an image of a longitudinal section of the optic nerve of mouse #4 that shows GAP-43-positive axons. FIG. 4D is an image of a longitudinal section of the optic nerve of mouse #10 that shows GAP-43-positive axons. Mice #3, #4, and #10 were treated with PSP-2 after ONC.

FIG. 6A is a bar plot showing that PSP-2 (50 µM) reduced metal autometallography (AMG) signal in the retina, day 1 post optic nerve crush (ONC). FIG. 6B provides cell images.

FIG. 7A is a bar plot showing that PSP-2 improved axon regeneration in a dose-dependent manner 2 weeks post optic nerve crush (ONC).

FIGS. 7C to 7Q are images.

DETAILED DESCRIPTION OF THE INVENTION

Figure 1:
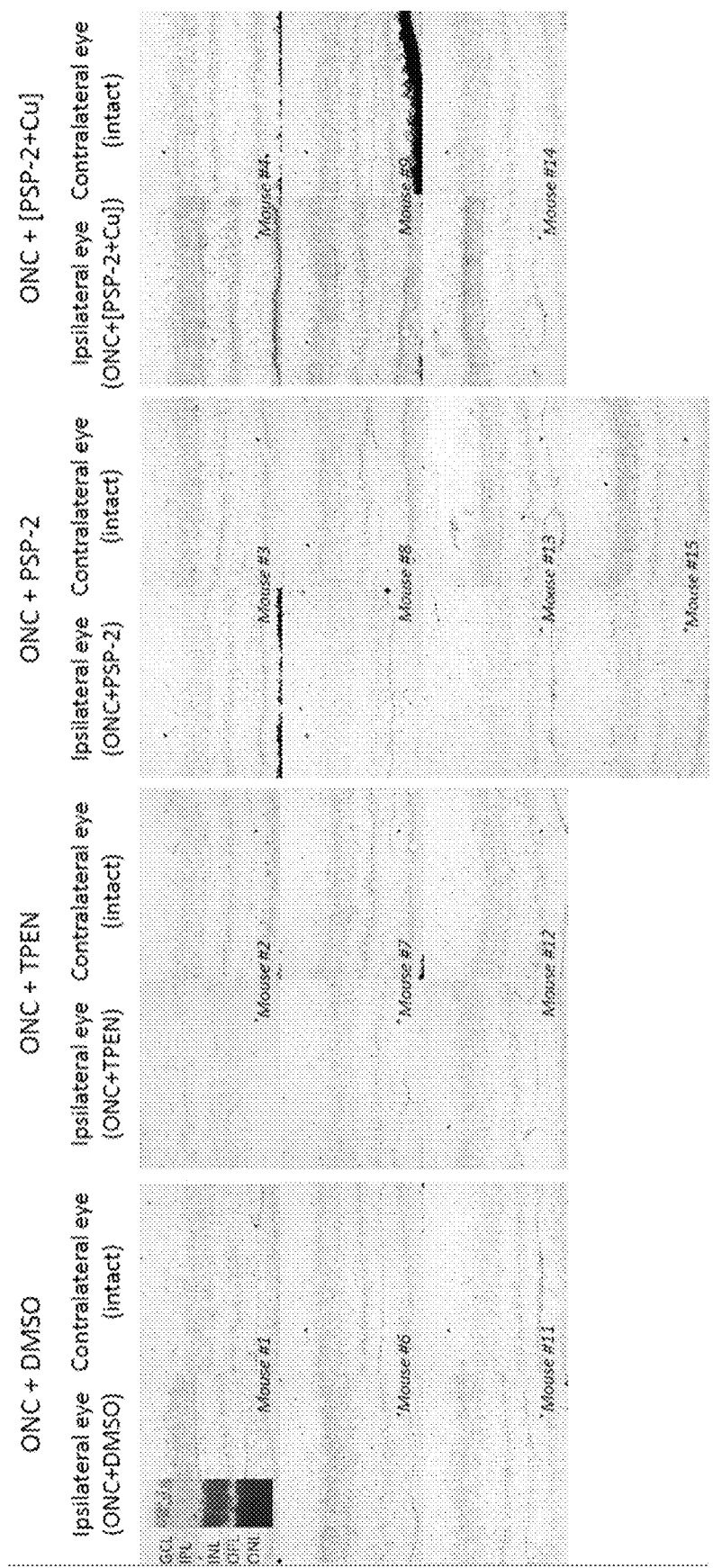
FIG. 1 includes autometallographic (AMG) images of the retinas of 15 mice on day-1 post optic nerve crush (ONC). The 15 mice were divided into four experimental groups. "ONC+DMSO" denotes treating ONC with a vehicle solution containing a phosphate buffered saline and 1% of dimethyl sulfoxide (DMSO). "ONC+TPEN" denotes treating ONC with N, N, N', N'-tetrakis(2-pyridylmethyl) ethylenediamine (TPEN). "ONC+PSP-2" denotes treating ONC with PSP-2. "ONC+[PSP-2+Cu]" denotes treating ONC with PSP-2 saturated with divalent copper.

As described below, the present invention features compositions and methods for treating neuronal injury or CNS lesion using a phosphine sulfide-stabilized phosphine.

The invention is based, at least in part, on the discovery that PSP-2, which is a high affinity copper chelator, promotes axonal regeneration in a murine model of central nervous system (CNS) injury.

Accordingly, the invention provides compositions comprising phosphine sulfide-stabilized phosphines (PSP) (e.g., PSP-1, PSP-2, phenPS, naphPS), and methods of using such compositions to treat neuronal injury and/or promote axon regeneration in connection with a central nervous system (CNS) lesion.

Neuronal injury and CNS lesions can result from a variety of insults. A neuronal injury or CNS lesion typically results from damage to one or more neurons. Such damage results in the loss of a neuron, or the loss of a part of the neuron (e.g., an axon). CNS lesion or neuronal injury may result from an acute or traumatic injury to the neuron as the result of trauma (e.g., acute spinal cord injury, traumatic brain injury, cortical impact). Acute traumatic injury can also result from an acute condition, such as stroke, that results in acute ischemia to the neuron resulting in acute damage. Neuronal injury or a CNS lesion may result from a surgical intervention or may occur during surgery as a consequence of hypoxia, for example.

Phosphine Sulfide-Stabilized Phosphines

The present invention is directed to phosphine sulfide-stabilized phosphines (PSP). PSPs are described, for example, by Morgan et al., PNAS, 116 (25): 12167-72 (2019) and Saeedifard et al, Inorg. Chem., May 24, 2019 doi.org/10.1021/acs.inorgchem.9b00965, the contents of each are incorporated herein by reference in their entirety. PSP-1 has a dissociation constant for copper of about 0.8 fM.

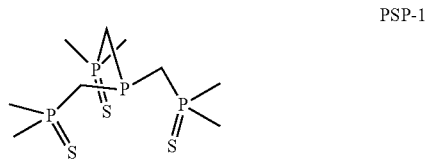

PSP-1

As reported in detail below, a high affinity copper chelator, PSP-2, promoted axon regeneration after neuronal injury in a murine optic nerve crush model. PSP-2 has the following structure:

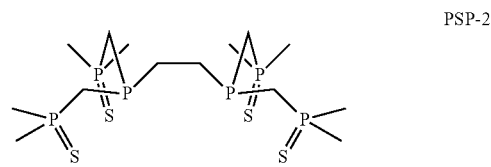

PSP-2

PSP-2 has a $10^{17}$ fold selectivity for copper over other transition metals (Morgan et al, Angew Chem Int Ed Engl., 57(31): 9711-15 (2018), the contents of which are incorporated herein by reference in their entirety).

PhenPS binds Cu(I) with a 1:1 stochiometry and a dissociation constant of about 0.6 zM. PhenPS has the following structure:

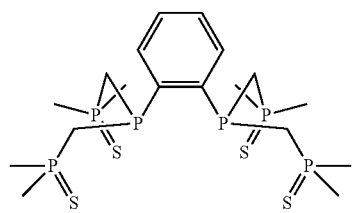

phenPS

In some embodiments, the PSP is a water-soluble acidic version of phenPS.

Like phenPS, naphPS binds Cu(I) with high affinity ($K_d$=0.8 zM).

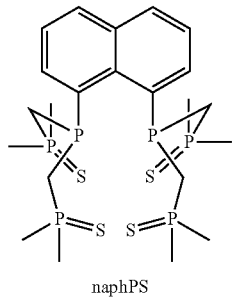

naphPS

In some embodiments, compositions are provided that comprise a phosphine sulfide-stabilized phosphine (e.g., PSP-1, PSP-2, phenPS, naphPS) and a pharmaceutically acceptable diluent, carrier, vehicle, or excipient. In other aspects, methods are provided for using a phosphine sulfide-stabilized phosphine to promote axon growth and neuron regeneration. In these methods, a neuron is contacted with a phosphine sulfide-stabilized phosphine (e.g., PSP-1, PSP-2, phenPS, naphPS). In some embodiments, the contacting is at or near a site of neuronal damage or injury. In some embodiments, contacting at the site of injury or damage means within 1 mm of the site of injury or damage. "Near" the injured or damaged site on the neuron refers herein to any distance from the injured or damaged site from which the neuron responds as intended (i.e., by exhibiting regeneration or axon growth).

Pharmaceutical Compositions

In some aspects, the present invention provides a pharmaceutical composition comprising a phosphine sulfide-stabilized phosphine (e.g., PSP-1, PSP-2, phenPS, naphPS). The pharmaceutical compositions of the present invention can be prepared in accordance with known techniques. See, e.g., Remington, *The Science and Practice of Pharmacy* (21st ed. 2005). In some embodiments, a phosphine sulfide-stabilized phosphine (e.g., PSP-1, PSP-2, phenPS, naphPS) is admixed with a suitable carrier prior to administration or storage, and in some embodiments, the pharmaceutical composition further comprises a pharmaceutically acceptable carrier. Suitable pharmaceutically acceptable carriers generally comprise inert substances that aid in administering the pharmaceutical composition to a subject, aid in processing the pharmaceutical compositions into deliverable preparations, or aid in storing the pharmaceutical composition prior to administration. Pharmaceutically acceptable carriers can include agents that can stabilize, optimize or otherwise alter the form, consistency, viscosity, pH, pharmacokinetics, solubility of the formulation. Such agents include buffering agents, wetting agents, emulsifying agents, diluents, encapsulating agents, and skin penetration enhancers. For example, carriers can include, but are not limited to, saline, buffered saline, dextrose, arginine, sucrose, water, glycerol, ethanol, sorbitol, dextran, sodium carboxymethyl cellulose, and combinations thereof.

In addition to a phosphine sulfide-stabilized phosphine (e.g., PSP-1, PSP-2, phenPS, naphPS) and the carrier, the pharmaceutical compositions of the present invention can include at least one additional therapeutic agent useful in the treatment of an injury, disease, or neurological condition. In some embodiments, the pharmaceutical compositions comprising a phosphine sulfide-stabilized phosphine (e.g., PSP-1, PSP-2, phenPS, naphPS) can be administered separately from an additional therapeutic agent.

The pharmaceutical compositions of the present invention can be used to treat any injury, disease, or neurological condition that is responsive to a phosphine sulfide-stabilized phosphine (e.g., PSP-1, PSP-2, phenPS, naphPS). The pharmaceutical compositions, in some embodiments are useful in the treatment of a neuronal injury. In some embodiments, the pharmaceutical compositions are useful in the treatment of an injury, disease, or neurological condition characterized by neuronal injury.

Pharmaceutical compositions of the present invention can comprise a therapeutically effective amount of a phosphine sulfide-stabilized phosphine (e.g., PSP-1, PSP-2, phenPS, naphPS), and this amount may vary for different subjects being treated. In one embodiment, between about 100 mg and 10,000 mg, between about 100 mg and 1000 mg, between about 100 mg and 500 mg, or 500 mg and 1000 mg of a phosphine sulfide-stabilized phosphine (e.g., PSP-1, PSP-2, phenPS, naphPS) are administered to a human subject. Determining the precise effective dose may be based on factors for each individual subject, including their size, age, sex, weight, and condition. Dosages can be readily ascertained by those skilled in the art from this disclosure and the knowledge in the art.

The skilled artisan can readily determine the amount of a phosphine sulfide-stabilized phosphine (e.g., PSP-1, PSP-2, phenPS, naphPS) and the amount of optional additives, vehicles, and/or carriers in the compositions of the present invention and to be administered in methods of the invention. Typically, additives are present in an amount of 0.001 to 50% (weight) solution in phosphate buffered saline, and the active ingredient is present in the order of micrograms to milligrams, such as about 0.0001 to about 5 wt %, preferably about 0.0001 to about 1 wt %, still more preferably about 0.0001 to about 0.05 wt % or about 0.001 to about 20 wt %, preferably about 0.01 to about 10 wt %, and still more preferably about 0.05 to about 5 wt %. Of course, for any composition to be administered to an animal or human, and for any particular method of administration, it is preferred to determine therefore: toxicity, such as by determining the lethal dose (LD) and LD50 in a suitable animal model (e.g., a rodent such as a mouse); and, the dosage of the composition(s), concentration of components therein, and the timing of administering the composition(s), which elicit a suitable response. Such determinations do not require undue experimentation from the knowledge of the skilled artisan, this disclosure and the documents cited herein.

In one embodiment, pharmaceutically acceptable formulations comprise a polymer for delivering an agent, such as a phosphine sulfide-stabilized phosphine (e.g., PSP-1, PSP-2, phenPS, naphPS), that promotes axon outgrowth, thereby treating an injury, disease, or neurological condition. In some embodiments, a polymer includes co-polymers, homopolymers, linear polymers, branched polymers, and cross-linked polymers. Polymers contemplated for use in the pharmaceutical compositions described herein include, but are not limited to, naturally derived biodegradable polymers that are compatible with the nervous system, such as albumin, alginate, cellulose derivatives, collagen, fibrin, gelatin, and polysaccharides, as well as synthetic polymers such as polyesters (PLA, PLGA), polyethylene glycol, poloxomers, polyanhydrides, cyclodextrins, and pluronics. Synthetic polymers are also contemplated. Polymers can be prepared using methods known in the art.

In some embodiments, a phosphine sulfide-stabilized phosphine (e.g., PSP-1, PSP-2, phenPS, naphPS) is encapsulated in one or more pharmaceutically acceptable polymers to form a microcapsule (also referred to as a microsphere or microparticle), which are typically free-flowing powders consisting of spherical particles of 2 mm or less in diameter. In some embodiments, the microcapsule, microsphere, or microparticle is 500 μm or less in diameter. Nanocapsules (also referred to as nanospheres or nonparticles) have diameters less than 1 μm.

In another embodiment, a pharmaceutically acceptable formulation comprising a phosphine sulfide-stabilized phosphine (e.g., PSP-1, PSP-2, phenPS, naphPS) is a lipid-based formulation. Lipid-based drug delivery systems are known in the art and can be used in the practice of the present invention. For example, multivesicular liposomes, multilamellar liposomes, and unilamellar liposomes are contemplated herein.

In some embodiments, the pharmaceutically acceptable formulation comprises a synthetic membrane vesicle. The synthetic membrane vesicle is usually a combination of phospholipids and steroids, especially cholesterol. Other phospholipids or lipids may also be used. For example, synthetic membrane vesicle can comprise phosphatidylglycerols, phosphatidylcholines, phosphatidylserines, phosphatidylethanolamines, sphingolipids, cerebrosides, and gangliosides, with preferable embodiments including egg phosphatidylcholine, dipalmitoylphosphatidylcholine, distearoylphosphatidyleholine, dioleoylphosphatidylcholine, dipalmitoylphosphatidylglycerol, and dioleoylphosphatidylglycerol.

Methods of Treatment

Some aspects of the present invention provide methods of treating a neuronal injury or CNS lesion by administering a composition comprising a phosphine sulfide-stabilized phosphine (e.g., PSP-1, PSP-2, phenPS, naphPS) to a subject in need thereof. In some embodiments, the subject has or is suspected of having a neuronal injury or CNS lesion. These methods comprise administering a pharmaceutical composition comprising an effective amount of a phosphine sulfide-stabilized phosphine (e.g., PSP-1, PSP-2, phenPS, naphPS) to a subject (e.g., a mammal such as a human). The method includes the step of administering to the mammal an effective amount of a phosphine sulfide-stabilized phosphine (e.g., PSP-1, PSP-2, phenPS, naphPS) sufficient to treat the injury or CNS lesion or symptom thereof, under conditions such that the injury or lesion is treated.

Administration of a phosphine sulfide-stabilized phosphine (e.g., PSP-1, PSP-2, phenPS, naphPS) can be systemic or site-specific (e.g., localized delivery at the site of injury). In one embodiment, the chelator is site-specifically administered to a subject in need thereof. For example, after a neuronal injury, a composition of the present invention comprising a phosphine sulfide-stabilized phosphine (e.g., PSP-1, PSP-2, phenPS, naphPS) is administered directly to the injured site in a subject.

In one embodiment, administration of the phosphine sulfide-stabilized phosphine (e.g., PSP-1, PSP-2, phenPS, naphPS) to a subject (e.g., in a single or in different pharmaceutical compositions, with or without an additional therapeutic agent) results in the phosphine sulfide-stabilized phosphine (e.g., PSP-1, PSP-2, phenPS, naphPS) directly contacting an injured neuron in need of regeneration (e.g., at the site of axonal injury or at the site of origin of the injured neuron). In one embodiment, administration results in contacting neurons proximal to a site of neuronal injury. In one embodiment, the administration is directly to an injured neuron (e.g., at the site of origin of the injured neuron or at the site of axonal injury). Such administration can be achieved by localized or systemic administration.

In some embodiments, the phosphine sulfide-stabilized phosphine (e.g., PSP-1, PSP-2, phenPS, naphPS) is administered orally. In some embodiments, the subject is administered a phosphine sulfide-stabilized phosphine (e.g., PSP-1, PSP-2, phenPS, naphPS) parenterally. "Parenteral administration", as used herein, means administration by any method other than through the digestive tract or non-invasive topical or regional routes. For example, parenteral administration may include administration to a patient intravenously, intradermally, intraarterially, intraperitoneally, intralesionally, intracranially, intraarticularly, intraprostatically, intrapleurally, intratracheally, intravitreally, intramuscularly, subcutaneously, subconjunctivally, intraocularly, intravesicularly, intrapericardially, intraumbilically, by injection, and by infusion. In one embodiment, the administration is suitable for treatment of spinal cord injury, e.g., by injection into the spinal column or spinal canal. In certain aspects of the invention, a therapeutic agent, such as a phosphine sulfide-stabilized phosphine (e.g., PSP-1, PSP-2, phenPS, naphPS), is introduced into a cerebral ventricle, the lumbar area, or the cisterna magna. In another aspect, the therapeutic agent is introduced locally, such as into the site of nerve or cord injury, into a site of pain, or intraocularly to contact neuroretinal cells.

Since regeneration and axonal generation in the treatment of a neuronal injury includes compensatory promotion of neuronal outgrowth of uninjured neurons, benefit is expected from mere delivery of the agent to an injury site. As such, suitable target neurons are actual damaged neurons, and also neurons that are in the immediate area of an injury site. The specific location and extent of an injury site can be determined by the skilled practitioner. Examples of injury sites are the site of physical damage or disruption of neuronal activity. The immediate area of an injury site will vary with respect to the specific injury, the nature of the injury, and the nature of the injured neurons (e.g., axonal length, specific function, etc.) and can be determined by the skilled practitioner. In one embodiment, the immediate area of the injury site is within about 1-10 mm of identified damaged neurons (e.g., 1, 2, 3, 4, 5, 6, 7, 8, 9, or 10 mm).

In one embodiment, the phosphine sulfide-stabilized phosphine (e.g., PSP-1, PSP-2, phenPS, naphPS) is administered within at least about 1, 2, 3, 4, 5, or 6 hours of the neuronal injury. In another embodiment, the phosphine sulfide-stabilized phosphine (e.g., PSP-1, PSP-2, phenPS, naphPS) is administered within at least about 8, 10, 12, or 24 hours of the neuronal injury. In some embodiments, the phosphine sulfide-stabilized phosphine (e.g., PSP-1, PSP-2, phenPS, naphPS) is administered within about 1, 2, or 3 days of the neuronal injury. In some embodiments, the phosphine sulfide-stabilized phosphine (e.g., PSP-1, PSP-2, phenPS, naphPS) is administered at the time a neuronal injury is diagnosed.

In some embodiments, administration of a phosphine sulfide-stabilized phosphine (e.g., PSP-1, PSP-2, phenPS, naphPS) or a composition comprising a phosphine sulfide-stabilized phosphine (e.g., PSP-1, PSP-2, phenPS, naphPS) can induce axon growth at or near the injured site with 5 to 20 days, within 5 to 15 days, or within 5 to 10 days. In some embodiments, administration of a phosphine sulfide-stabilized phosphine (e.g., PSP-1, PSP-2, phenPS, naphPS) or a composition comprising a phosphine sulfide-stabilized phosphine (e.g., PSP-1, PSP-2, phenPS, naphPS) can induce axon growth at or near the injured site within 10 to 20 days or within 15 to 20 days.

Evaluating Efficacy

Methods for evaluating the efficacy of treatment are known in the art. In one approach, regeneration is evaluated by determining and comparing the number of neurons (injured and also uninjured) present at a site, and by detecting axonal outgrowth from the neurons following treatment with a phosphine sulfide-stabilized phosphine (e.g., PSP-1, PSP-2, phenPS, naphPS), as compared to the number of neurons and the axonal outgrowth in the absence of such treatment. In some embodiments, cell survival and regeneration are evaluated by determining and comparing the number of neurons (injured and also uninjured) present at a site, and by detecting the numbers of axons extending from the neurons following treatment with a PSP, as compared to the number of neurons and the axonal outgrowth in the absence of such treatment. Regeneration and axonal outgrowth occurs if greater than 1% (e.g., 1.5%, 2%, 5%, 10%, 15%, 20%, 25%, 30%, 35%, 0%, 45%, 50%, 55%, 60%, 65%, 70% and 75% or any percentage in between) of the neurons regenerate injured axons or generate new axons, that extend at least about 1-5 mm distal to the site of injury or lesion. In one embodiment, greater than 1% (e.g., 1.5%, 2%, 5%, 10%, 15%, 20%, 25%, 30%, 35%, 0%, 45%, 50%, 55%, 60%, 65%, 70% and 75% or any percentage in between) of neurons regenerate injured axons or generate axons over 1 mm distal to the lesion site. In one embodiment, greater than 1% (e.g., 11.5%, 2%, 5%, 10%, 15%, 20%, 25%, 30%, 35%, 0%, 45%, 50%, 55%, 60%, 65%, 70% and 75% or any percentage in between) of neurons regenerate or generate new axons that extend at least 2 mm distal from the lesion site. Other tests that may be used to determine the ability of an agent to produce neuronal outgrowth in a subject include standard tests of neurological function in human subjects or in animal models of spinal injury (such as standard reflex testing, urologic tests, urodynamic testing, tests for deep and superficial pain appreciation, proprioceptive placing of the hind limbs, ambulation, and evoked potential testing). In addition, nerve impulse conduction can be measured in a subject, such as by measuring conduct action potentials, as an indication of efficacy.

Animal models suitable for use in the assays of the present invention include the rat model of partial transaction (described in Weidner et al., (2001) Proc Natl Acad Sci USA 98:3513-3518). This animal model tests how well a compound can enhance the survival and sprouting of the intact remaining fragment of an almost fully-transected cord. Accordingly, after administration of a candidate agent these animals may be evaluated for recovery of a certain function, such as how well the rats may manipulate food pellets with their forearms (to which the relevant cord had been cut 97%).

Another animal model suitable for use in the assays of the present invention includes the rat model of stroke as described by Kawamata et al., ((1997) Proc Natl Acad Sci USA 94:8179-8184), which describes in detail various tests that may be used to assess sensor motor function in the limbs as well as vestibulomotor function after an injury. Administration to these animals of the agents described herein can be used to assess whether a given compound, route of administration, or dosage results in neuronal outgrowth or a neurosalutary effects, such as increasing the level of function, or increasing the rate of regaining function or the degree of retention of function in the test animals.

Standard neurological evaluations used to assess progress in human patients after a stroke may also be used to evaluate the ability of an agent to produce a neurosalutary effect in a subject. Such standard neurological evaluations are routine in the medical arts, and are described in, for example, "Guide to Clinical Neurobiology" Edited by Mohr and Gautier (Churchill Livingstone Inc. 1995).

Delivery of Therapeutic Agents

In one embodiment, the phosphine sulfide-stabilized phosphine (e.g., PSP-1, PSP-2, phenPS, naphPS) is administered into a subject intrathecally. As used herein, the term "intrathecal administration" is intended to include delivering an active compound formulation directly into the cerebrospinal fluid of a subject, by techniques including lateral cerebroventricular injection through a burr hole or cisternal or lumbar puncture or the like (described in Lazorthes et al., 1991, and Ommaya A. K., 1984, the contents of which are incorporated herein by reference). The term "lumbar region" is intended to include the area between the third and fourth lumbar (lower back) vertebrae. The term "cisterna magna" is intended to include the area where the skull ends and the spinal cord begins at the back of the head. In some embodiments, administration of a therapeutic agent to any of the above-mentioned sites can be achieved by direct injection of the active compound formulation or using infusion pumps. Implantable or external pumps and catheter may be used.

In one embodiment of the invention, the formulation is administered by lateral cerebroventricular injection into the brain of a subject, preferably within 100 hours of when an injury (resulting in a condition characterized by aberrant axonal outgrowth of central nervous system neurons) occurs (such as within 6, 12, or 24 hours of the time of the injury). The injection can be made, for example, through a burr hole made in the subject's skull. In another embodiment, the formulation is administered through a surgically inserted shunt into the cerebral ventricle of a subject, preferably within 100 hours of when an injury occurs (such as within 6, 12 or 24 hours of the time of the injury). For example, the injection can be made into the lateral ventricles, which are larger, even though injection into the third and fourth smaller ventricles can also be made. In yet another embodiment, the formulation is administered by injection into the cisterna magna, or lumbar area of a subject, preferably within 100 hours of when an injury occurs (such as within 6, 12, or 24 hours of the time of the injury).

An additional means of administration to intracranial tissue involves application of compounds of the invention to the olfactory epithelium, with subsequent transmission to the olfactory bulb and transport to more proximal portions of the brain. Such administration can be by nebulized or aerosolized preparations.

In a further embodiment, formulations for ophthalmic administration are used to prevent or reduce damage to retinal and optic nerve head tissues, as well as to enhance functional recovery after damage to ocular tissues. Ophthalmic conditions that may be treated include, but are not limited to, retinopathies (including diabetic retinopathy and retrolental fibroplasia), macular degeneration, ocular ischemia, glaucoma. Other conditions to be treated with the methods of the invention include damage associated with injuries to ophthalmic tissues, such as ischemia reperfusion injuries, photochemical injuries, and injuries associated with ocular surgery, particularly injuries to the retina or optic nerve head by exposure to light or surgical instruments. The ophthalmic formulation may be used as an adjunct to ophthalmic surgery, such as by vitreal or subconjunctival injection following ophthalmic surgery. In some embodiments, ophthalmic formulation is administered by intraocular, intravitreal, subconjunctival, or retrobulbar injections. In some embodiments, the ophthalmic formulation is administered as eye drops or an ointment. The formulation may be used for acute treatment of temporary conditions, or may be administered chronically disease. The ophthalmic formulation may also be used prophylactically, especially prior to ocular surgery or noninvasive ophthalmic procedures or other types of surgery.

In one embodiment, the therapeutic agents described herein are contacted with the neuron using an implantable device that contains the therapeutic agent and that is specifically adapted for delivery to a neuron. Examples of devices include solid or semi-solid devices such as controlled release biodegradable matrices, fibers, pumps, stents, adsorbable gelatin (e.g. Gelfoam), etc. The device may be loaded with premeasured, discrete and contained amounts of the agents sufficient to promote regeneration and/or survival of the neuron. In one embodiment, the device provides continuous contact of the neuron with the agent at nanomolar or micromolar concentrations, (e.g., for at least 2, 5, or 10 days, or for at least 2, 3, or 4 weeks, or for greater than 4 weeks, e.g., 5, 6, 7, or 8 weeks).

In one embodiment, the agent is contacted in vivo by introduction into the central nervous system of a subject, e.g., into the cerebrospinal fluid of the subject. In certain aspects of the invention, the agent is introduced intrathecally, e.g., into a cerebral ventricle, the lumbar area, or the cisterna magna. In another aspect, the agent is introduced intraocularly, to thereby contact retinal ganglion cells or the optic nerve. Modes of administration are described in U.S. Pat. No. 7,238,529.

In one embodiment of the invention, the therapeutic agent is administered by lateral cerebro ventricular injection into the brain of a subject in the inclusive period from the time of the injury to a time determined by the skilled practitioner (e.g., 100 hours). The injection can be made, for example, through a burr hole made in the subject's skull. In another embodiment, said encapsulated therapeutic agent is administered through a surgically inserted shunt into the cerebral ventricle of a subject in the inclusive period from the time of the injury to a time determined by the skilled practitioner (e.g., 100 hours thereafter). For example, the injection can be made into the lateral ventricles, which are larger, even though injection into the third and fourth smaller ventricles can also be made.

In yet another embodiment, the therapeutic agent is administered by injection into the cisterna magna, or lumbar area of a subject in the inclusive period from the time of the injury to a time determined by the skilled practitioner (e.g., 100 hours thereafter). Administration can be continuous, or can be by repeated doses.

In one embodiment, the repeated doses are formulated so that an effective amount of the therapeutic agent is continually present at the injury site.

In one embodiment, the therapeutic composition is administered to a subject for an extended period of time to produce optimum neuronal outgrowth. Sustained contact with the active compound can be achieved by, for example, repeated administration of the active compound over a period of time, such as one week, several weeks, one month or longer. More preferably, the formulation used to administer the active compound provides sustained delivery, such as "slow release" of the active compound to a subject. For example, the formulation may deliver the active compound for at least one, two, three, or four weeks after the formulation is administered to the subject. Preferably, a subject to be treated in accordance with the present invention is treated with the formulation for at least 30 days (either by repeated administration or by use of a sustained delivery system, or both).

As used herein, the term "sustained delivery" is intended to include continual delivery of the therapeutic agent in vivo over a period of time following administration, preferably at least several days, a week, several weeks, one month or longer. Sustained delivery of the therapeutic agent can be demonstrated by, for example, the continued therapeutic effect of the active compound over time (such as sustained delivery of the agents can be demonstrated by continued axonal growth in CNS neurons in a subject). Alternatively, sustained delivery of the therapeutic agent may be demonstrated by detecting the presence of the active agent in vivo over time.

Preferred approaches for sustained delivery include use of a polymeric capsule, a minipump to deliver the formulation, a biodegradable implant. Implantable infusion pump systems (such as Infusaid) and osmotic pumps (sold by Alza Corporation) are available in the art. Another mode of administration is via an implantable, externally programmable infusion pump. Suitable infusion pump systems and reservoir systems are also described in U.S. Pat. No. 5,368,562 by Blomquist and U.S. Pat. No. 4,731,058 by Doan, developed by Pharmacia Deltec Inc.

In one embodiment, a phosphine sulfide-stabilized phosphine (e.g., PSP-1, PSP-2, phenPS, naphPS) is delivered via a device for promoting regeneration at a CNS lesion or near an injured neuron. The device may be implantable into the subject. The device may have a reservoir loaded with a premeasured and contained amount of the therapeutic formulation comprising the phosphine sulfide-stabilized phosphine (e.g., PSP-1, PSP-2, phenPS, naphPS). Examples of devices include solid or semi-solid devices, such as controlled release biodegradable matrices, fibers, pumps, stents, adsorbable gelatin (e.g. Gelfoam), etc. The device may be loaded with premeasured, discrete and contained amounts of the therapeutic agent sufficient to promote regeneration of the neuron. In one embodiment, the device provides continuous contact of the neuron with the agent at nanomolar or micromolar concentrations (e.g., for at least 2, 5, or 10 days, or for at least 2, 3, or 4 weeks, or for greater than 4 weeks, e.g., 5, 6, 7, or 8 weeks).

Kits

The invention provides kits for the treatment of a neuronal injury or for promoting axonal outgrowth. In one embodiment, the kit includes a pharmaceutical pack comprising an effective amount of a phosphine sulfide-stabilized phosphine (e.g., PSP-1, PSP-2, phenPS, naphPS). In some embodiments, the effective amount of a phosphine sulfide-stabilized phosphine (e.g., PSP-1, PSP-2, phenPS, naphPS) is present in a pharmaceutical composition. In some embodiments, kit includes a pharmaceutical pack comprising an effective amount of a phosphine sulfide-stabilized phosphine (e.g., PSP-1, PSP-2, phenPS, naphPS) and an additional therapeutic agent. In some embodiments, a phosphine sulfide-stabilized phosphine (e.g., PSP-1, PSP-2, phenPS, naphPS) and the additional therapeutic agent are present or co-formulated in a pharmaceutical composition. In some embodiments, a phosphine sulfide-stabilized phosphine (e.g., PSP-1, PSP-2, phenPS, naphPS) and the additional pharmaceutic agent are present in separate pharmaceutical compositions that may be co-administered or administered at predetermined times. In some embodiments, the compositions are in unit dosage form. In some embodiments, the kit comprises a sterile container which contains a therapeutic or prophylactic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired, the kit further provides instructions for administering a phosphine sulfide-stabilized phosphine (e.g., PSP-1, PSP-2, phenPS, naphPS) to a subject having or suspected of having a neuronal injury. The instructions will generally include information about the use of a phosphine sulfide-stabilized phosphine (e.g., PSP-1, PSP-2, phenPS, naphPS) for the treatment of neuronal injuries. In other embodiments, the instructions include at least one of the following: description of a phosphine sulfide-stabilized phosphine (e.g., PSP-1, PSP-2, phenPS, naphPS) or the combination of a phosphine sulfide-stabilized phosphine (e.g., PSP-1, PSP-2, phenPS, naphPS) and at least one additional therapeutic agent; dosage schedule and administration for treatment of a neuronal injury; precautions; warnings; indications; counter-indications; over-dosage information; adverse reactions; animal pharmacology; clinical studies; and/or references. The instructions may be printed directly on the container (when present), or as a label applied to the container, or as a separate sheet, pamphlet, card, or folder supplied in or with the container.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Presence of Copper in Retina after Optic Nerve Injury

Copper is an essential trace nutrient for most forms of life and plays critical roles in fundamental biological processes, including respiration, iron acquisition, and connective tissue formation. In mammalian cells, a complex network of membrane transporters, cytosolic metallochaperones, and storage proteins is responsible for acquiring, distributing, and regulating cellular copper levels. Intriguingly, copper deficiency has sometimes been associated with acute optic neuropathy. To investigate the role of copper in nerve injury, a mouse model of nerve injury, optic nerve crush (ONC), was used.

Metals in the retina, i.e., copper and zinc, were visualized using autometallography. Prior to injury, autometallography (AMG) revealed only modest levels of metals in the normal retina. Interestingly, 1 day after optic nerve crush (NC), an increase in metals was observed. To determine whether copper chelators had any effect on this increase, the selective copper chelator PSP-2 was used. Mice were administered 3 µL of DMSO 1% in PBS (control), 100 µM TPEN (10 mM TPEN stock in DMSO diluted in PBS (DMSO 1%)), 50 µM PSP-2 (5 mM PSP-2 stock in DMSO diluted in PBS (DMSO 1%)), or 50 µM PSP-2+Cu (10 mM PSP-2+Cu in de-O2 water diluted in PBS (DMSO 1%) immediately after unilateral optic nerve crush (ONC). In these studies, the normal, intact retina was used as a reference.

Figure 2:
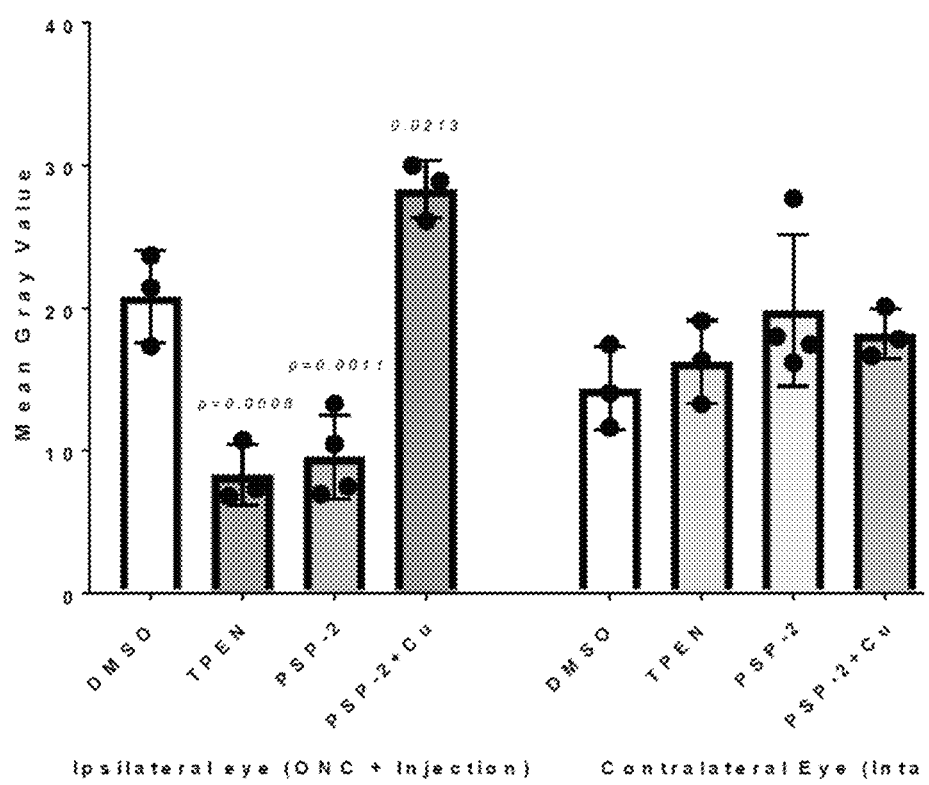
FIG. 2 is a graph quantifying the autometallographic results obtained from the images in FIG. 1.

Administration of a non-specific chelator, TPEN, and a copper chelator, PSP-2, reduced the autometallography signal in the retina one-day post ONC (FIGS. 1 and 2). Administration of PSP-2 and copper (PSP-2+Cu) abrogated the effectiveness of PSP-2 and induced further elevation of the AMG signal (FIGS. 1 and 2). These results show that the autometallography signal in the retina are metals including copper or that the autometallography signal is copper dependent. These results also show that shortly after injury Copper is present at or near injured neurons.

Example 2: PSP 2 Promotes Axon Regeneration

Figure 3A:
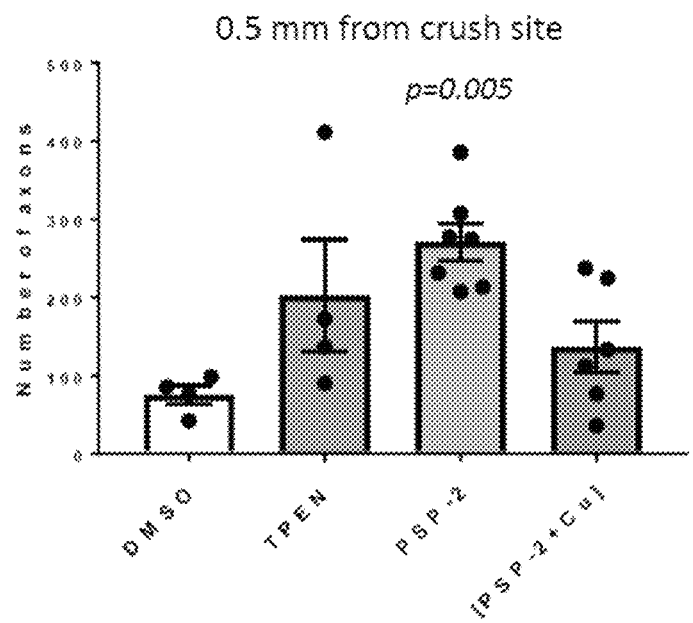
FIGS. 3A and 3B illustrate increased axon numbers in mice retinas after PSP-2 treatment of ONC.
Figure 3B:
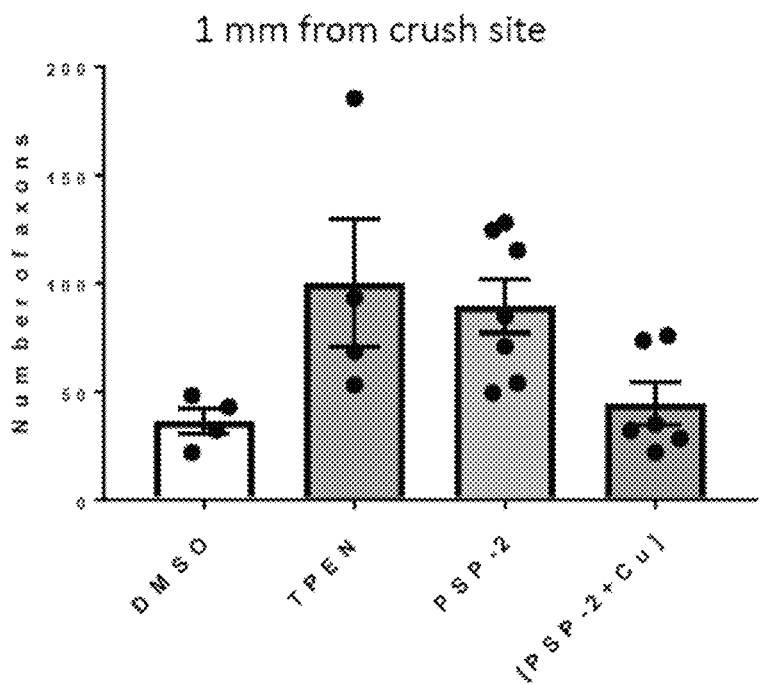
Figure 4A:
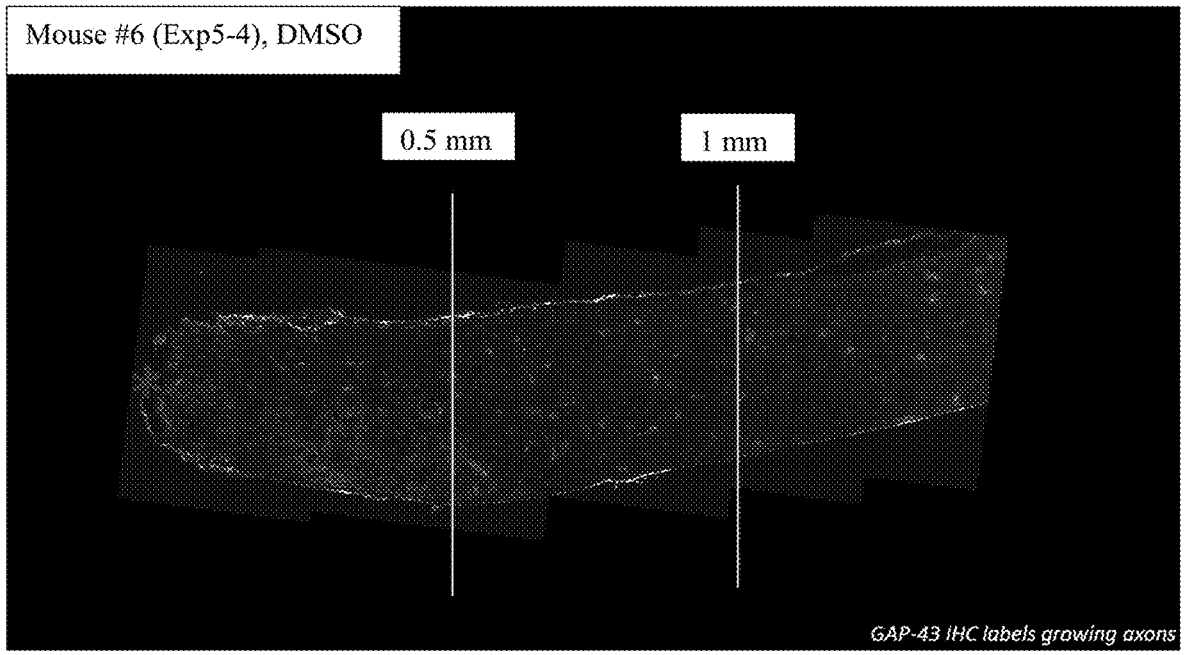
FIGS. 4A to 4D illustrate axon regeneration in the optic nerve in mice after PSP-2 treatment of ONC. For each figure, asterisks denote the site of ONC.
Figure 4B:
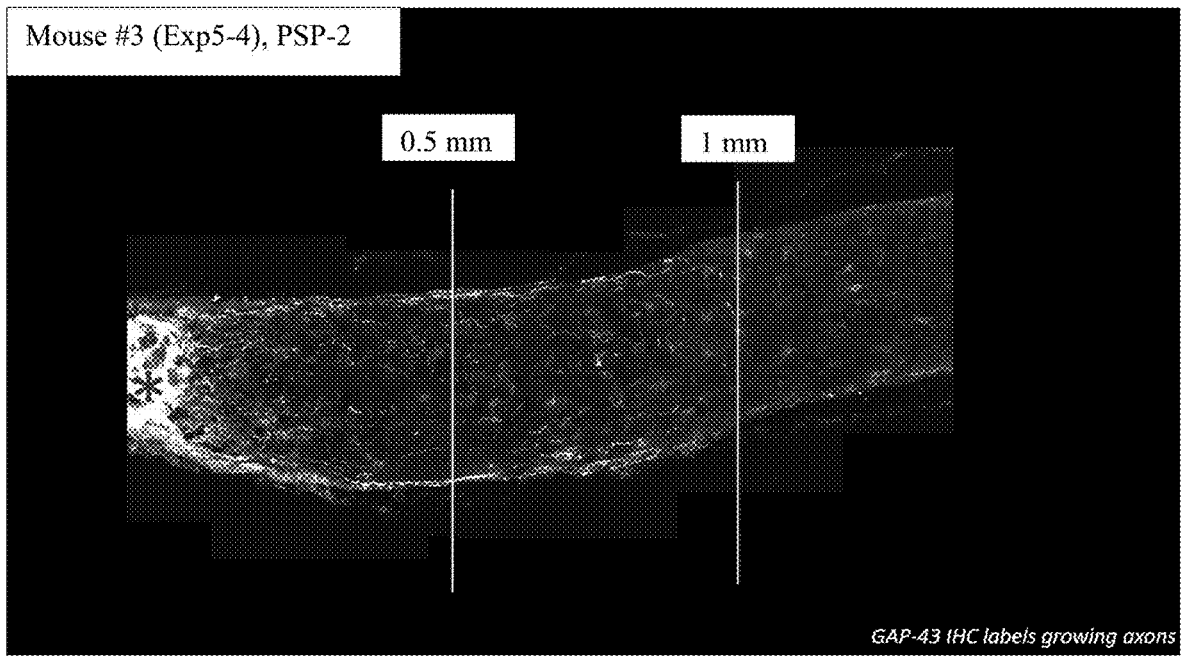
Figure 4C:
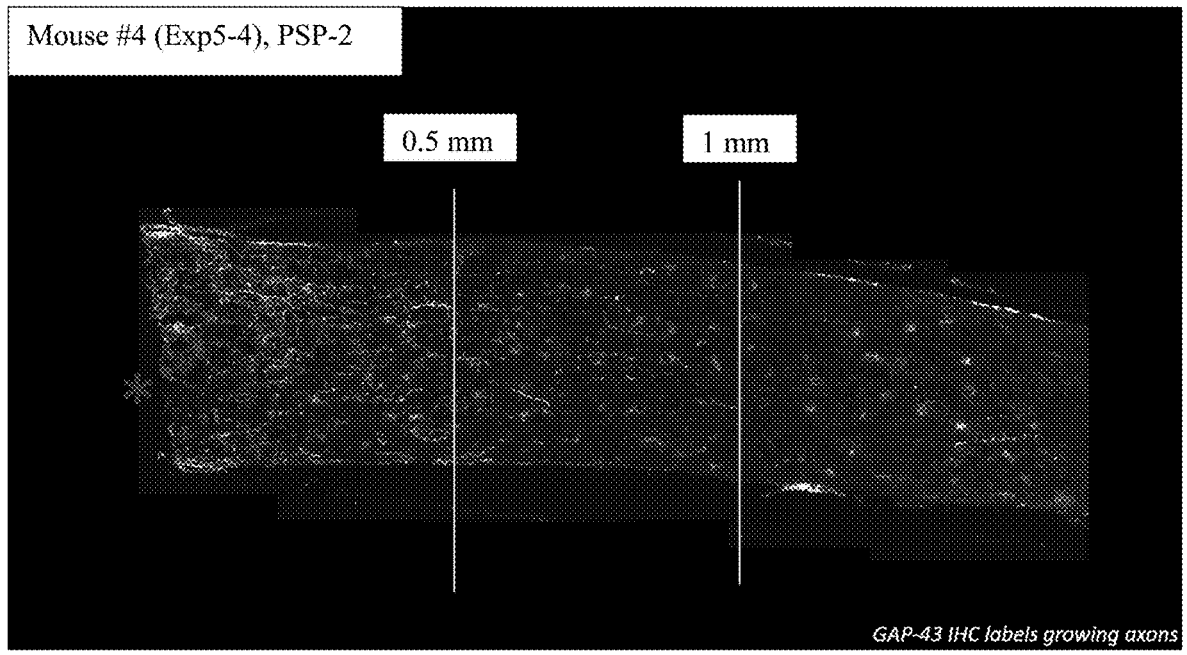
Figure 4D:
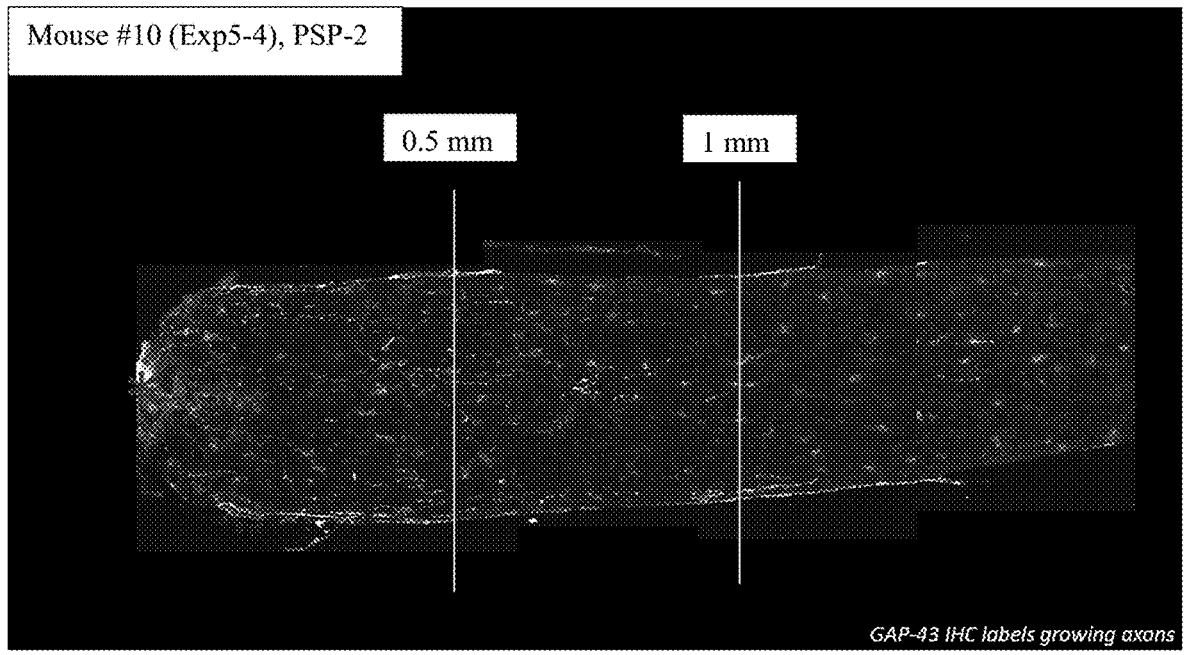
Figure 5:
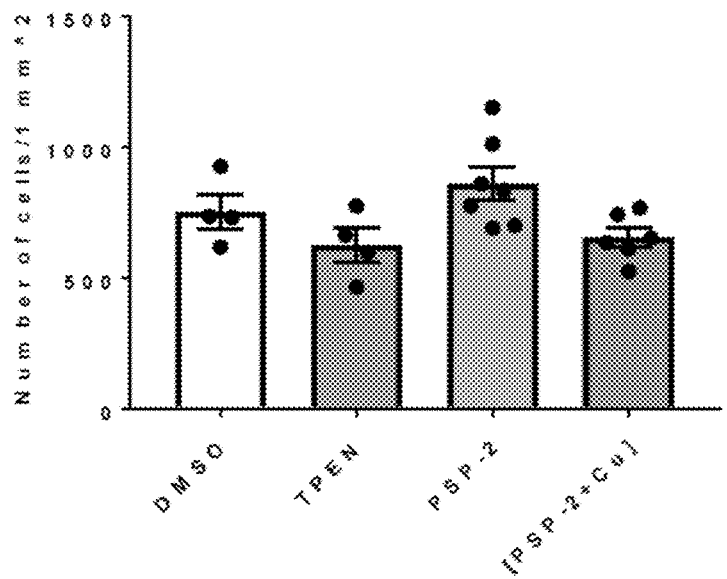
FIG. 5 is a graph that shows retinal ganglion cell (RGC) survival as the average number of βIII-tubulin positive RGCs axons per $mm^2$ in the retinas of mice treated with DMSO, TPEN, PSP-2, and PSP-2 saturate with divalent copper. Data for individual mice are represented by dots.

To determine if copper chelation promotes axon regeneration after nerve injury, mice were administered treatments as described in Example 1 after bilateral ONC. Referring to FIGS. 3A and 3B, PSP-2 administration improved axon regeneration at two weeks post ONC at both a 0.5 mm and a 1.0 mm distance from the site of ONC. An antibody against GAP-43 was used to detect growing axons (FIG. 4A-4D). PSP-2 promoted axon regeneration within two weeks post ONC, but did not significantly affect survival of retinal ganglion cells (FIG. 5).

Figure 6A:
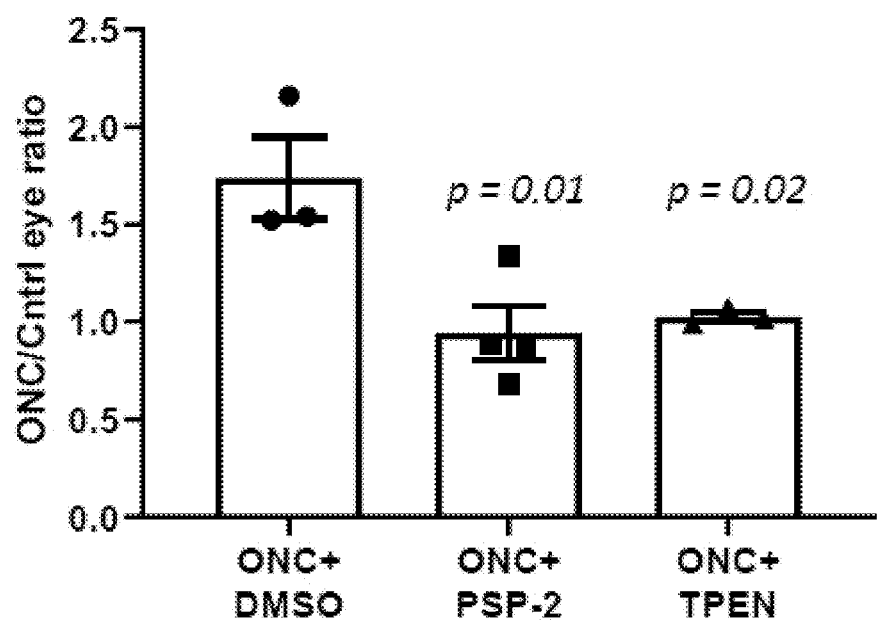
FIGS. 6A and 6B are a bar plot and images.
Figure 6B:
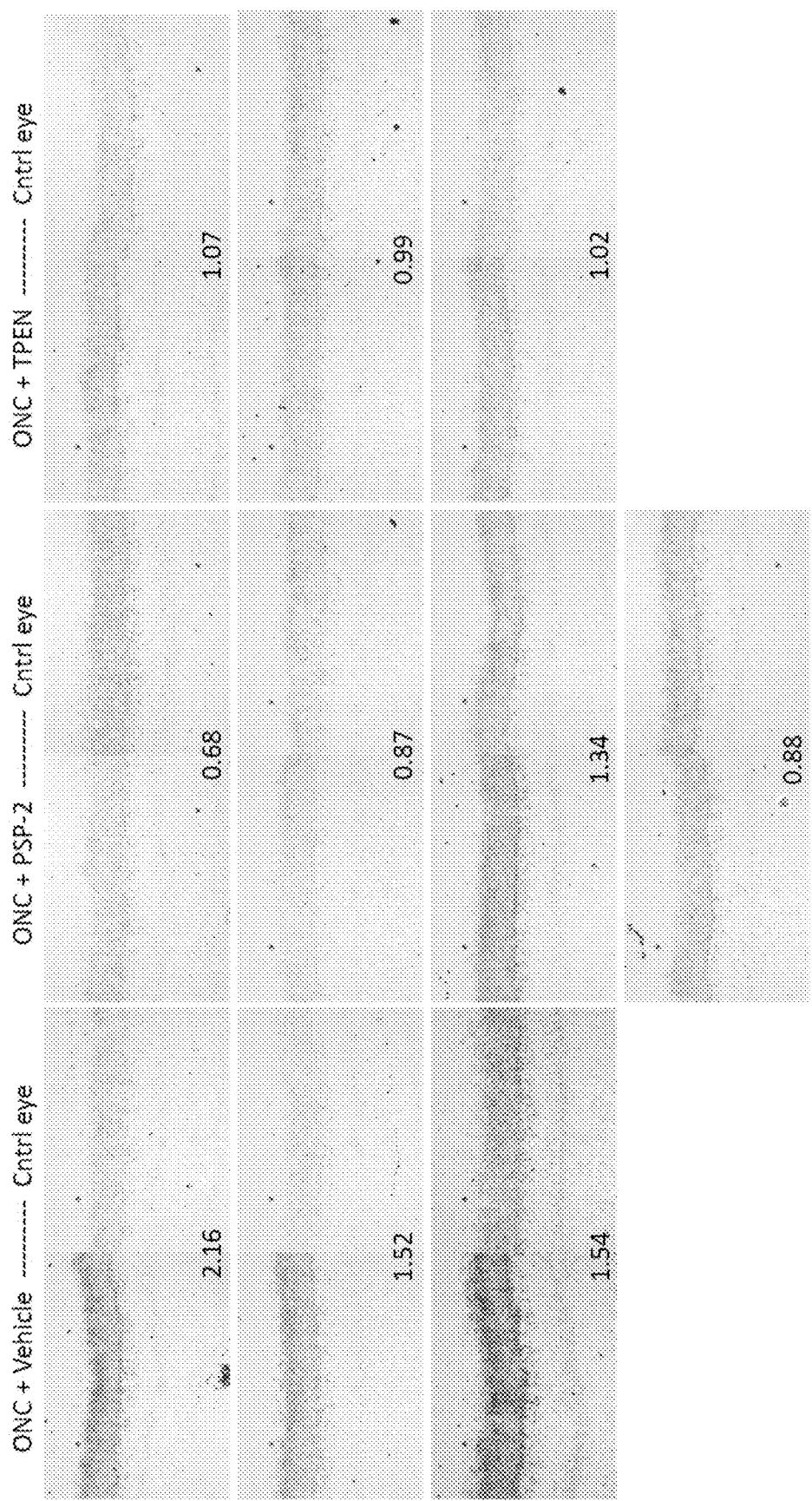
Figure 7A:
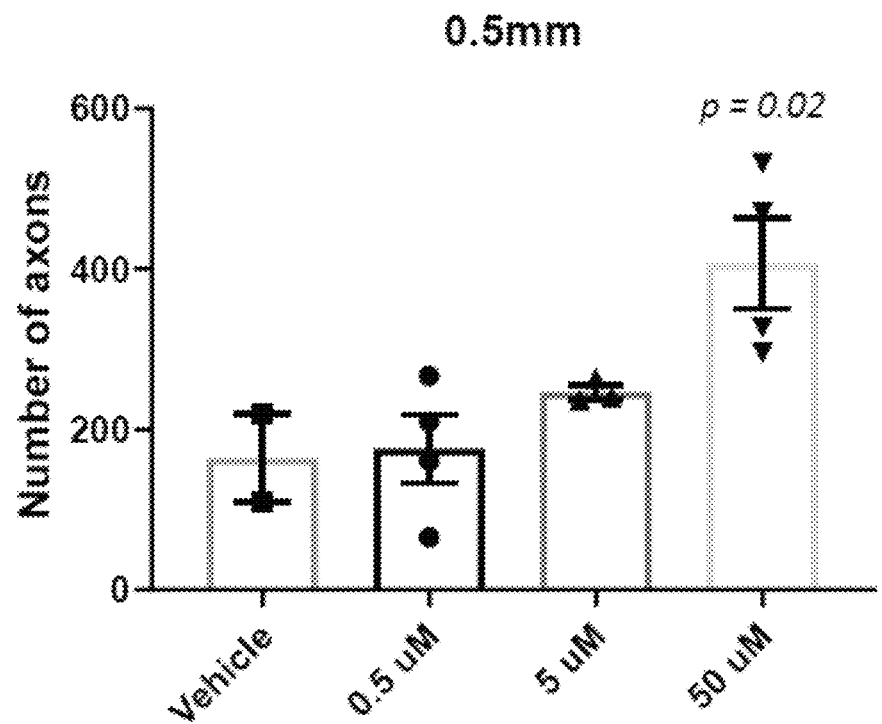
FIGS. 7A to 7Q are bar plots and images.
Figure 7B:
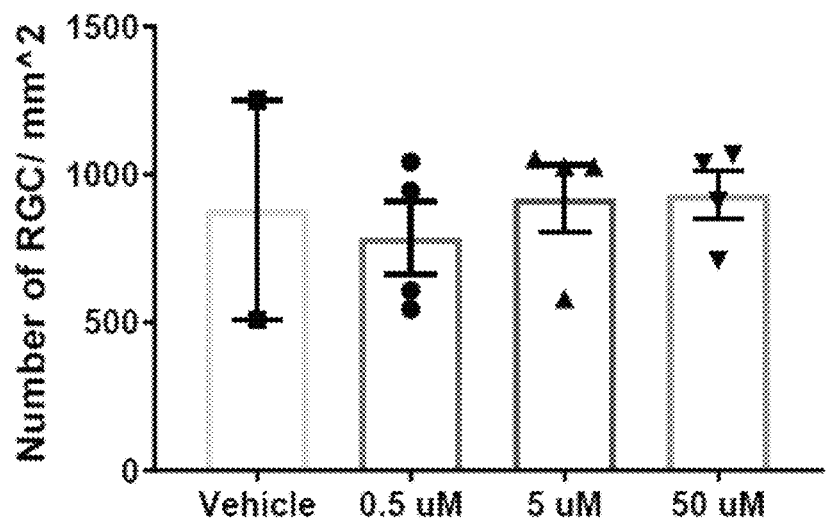
FIG. 7B is a bar plot showing that PSP-2 did not improve retinal ganglion cell (RGC) survival 2 weeks post optic nerve crush (ONC).
Figure 7C:
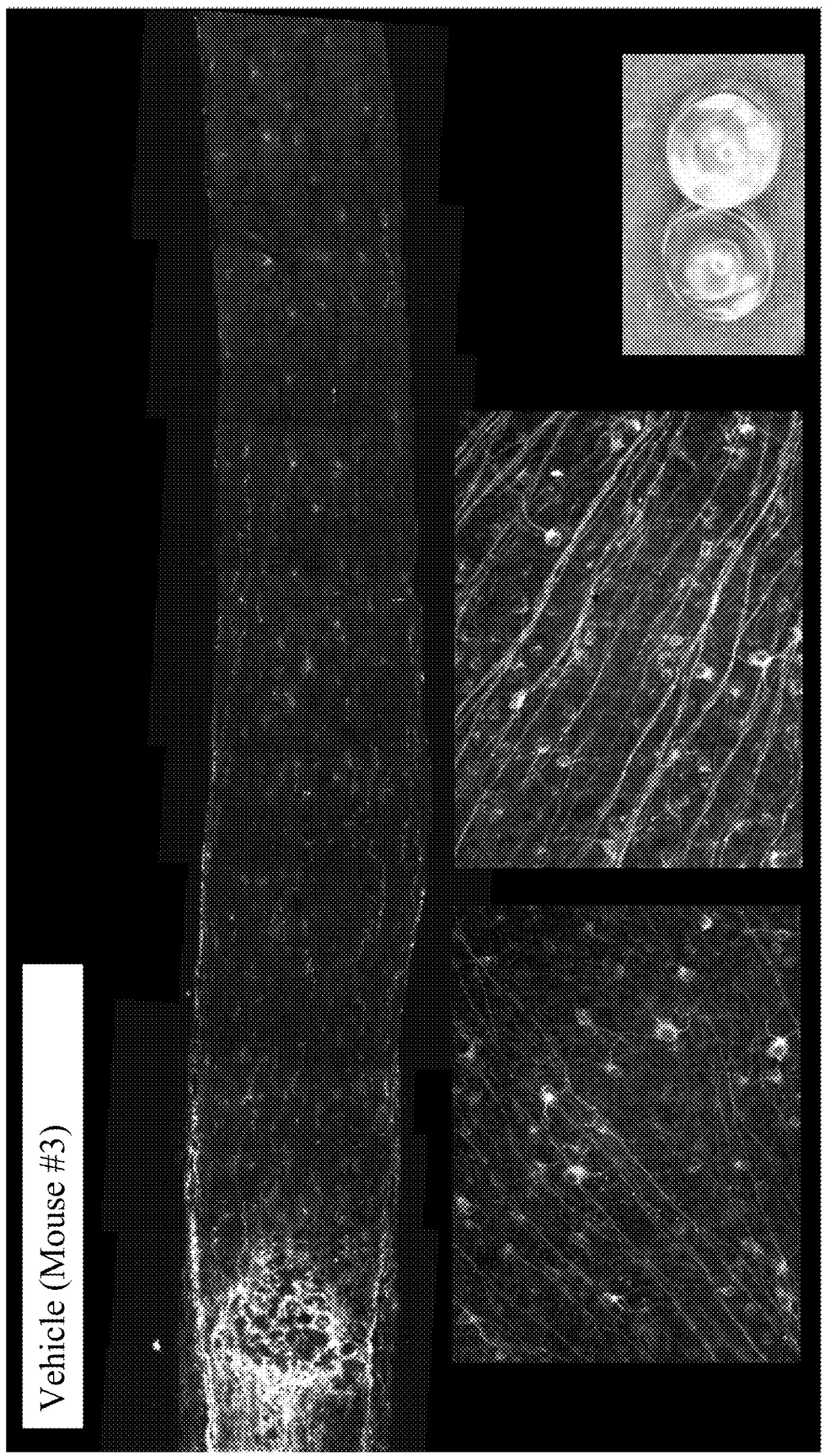
Figure 7D:
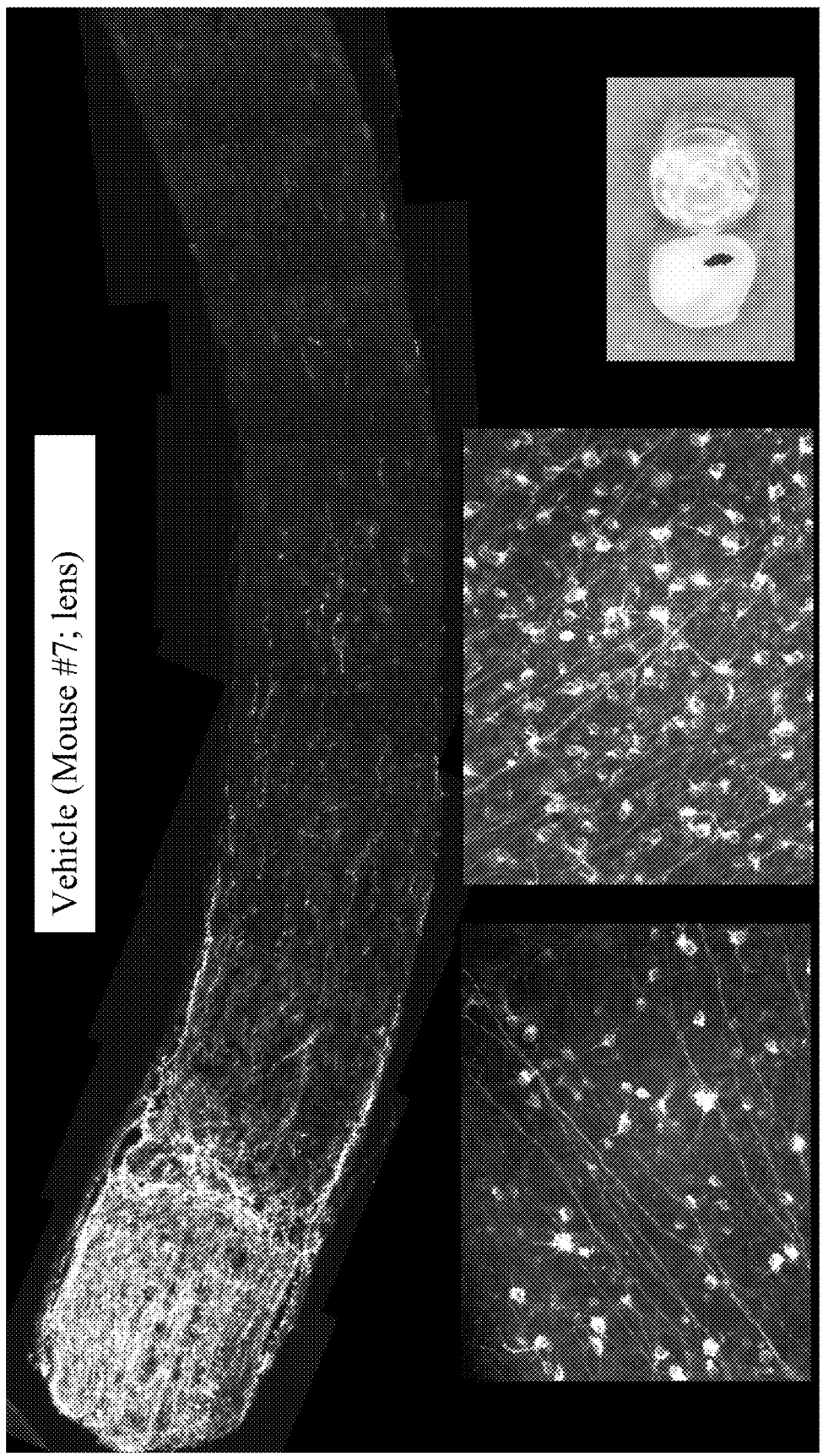
Figure 7E:
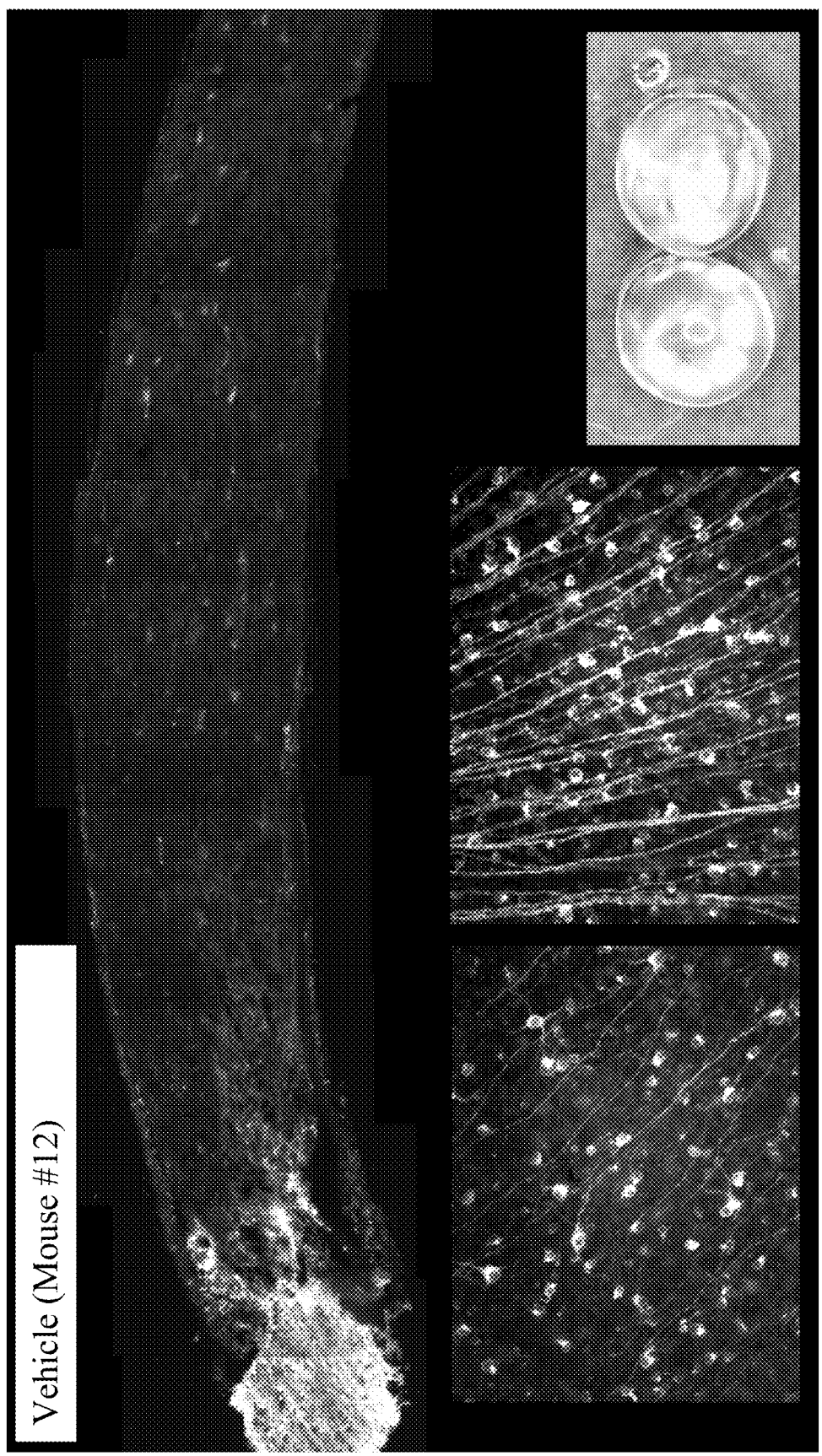
Figure 7F:
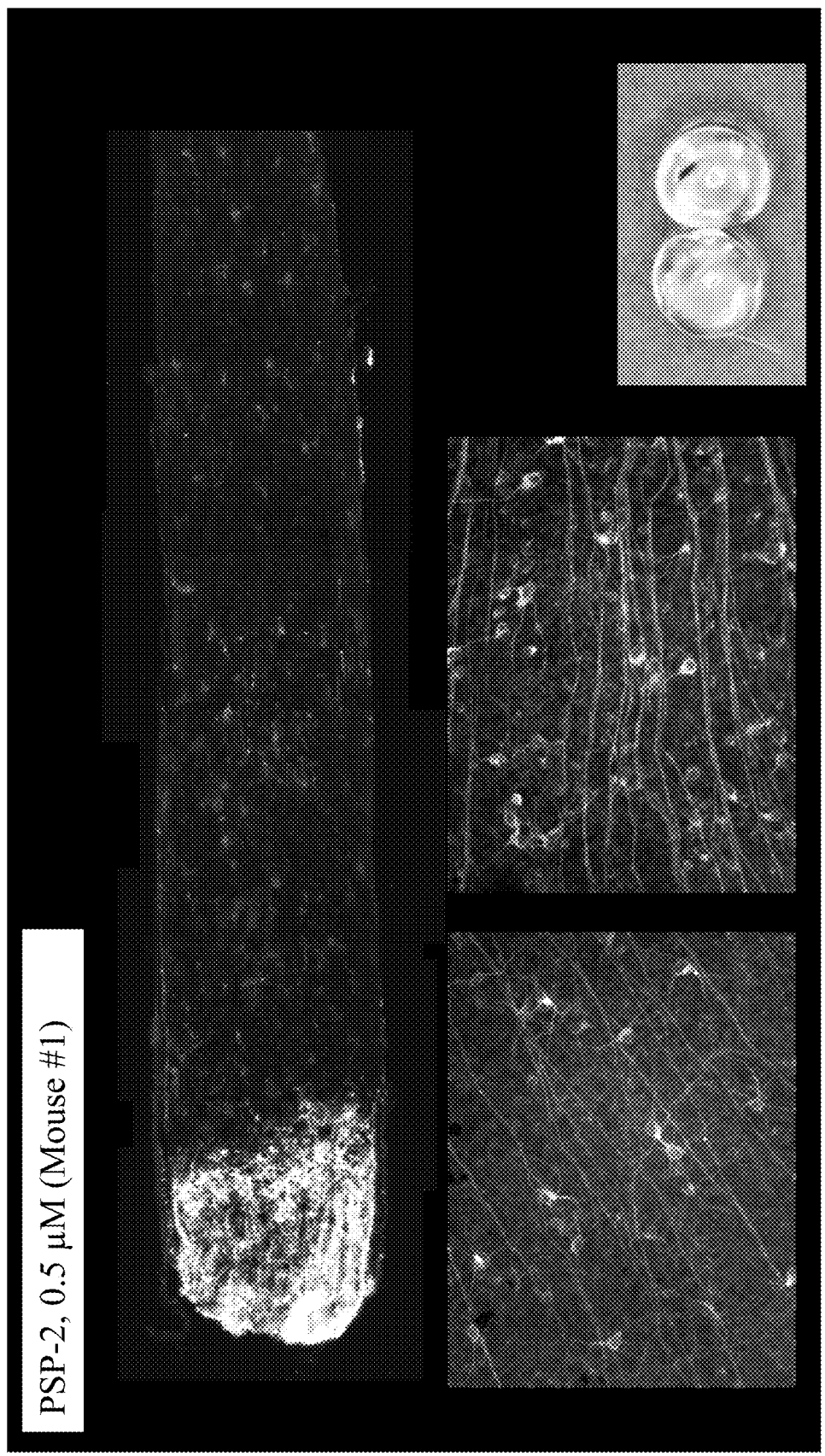
Figure 7G:
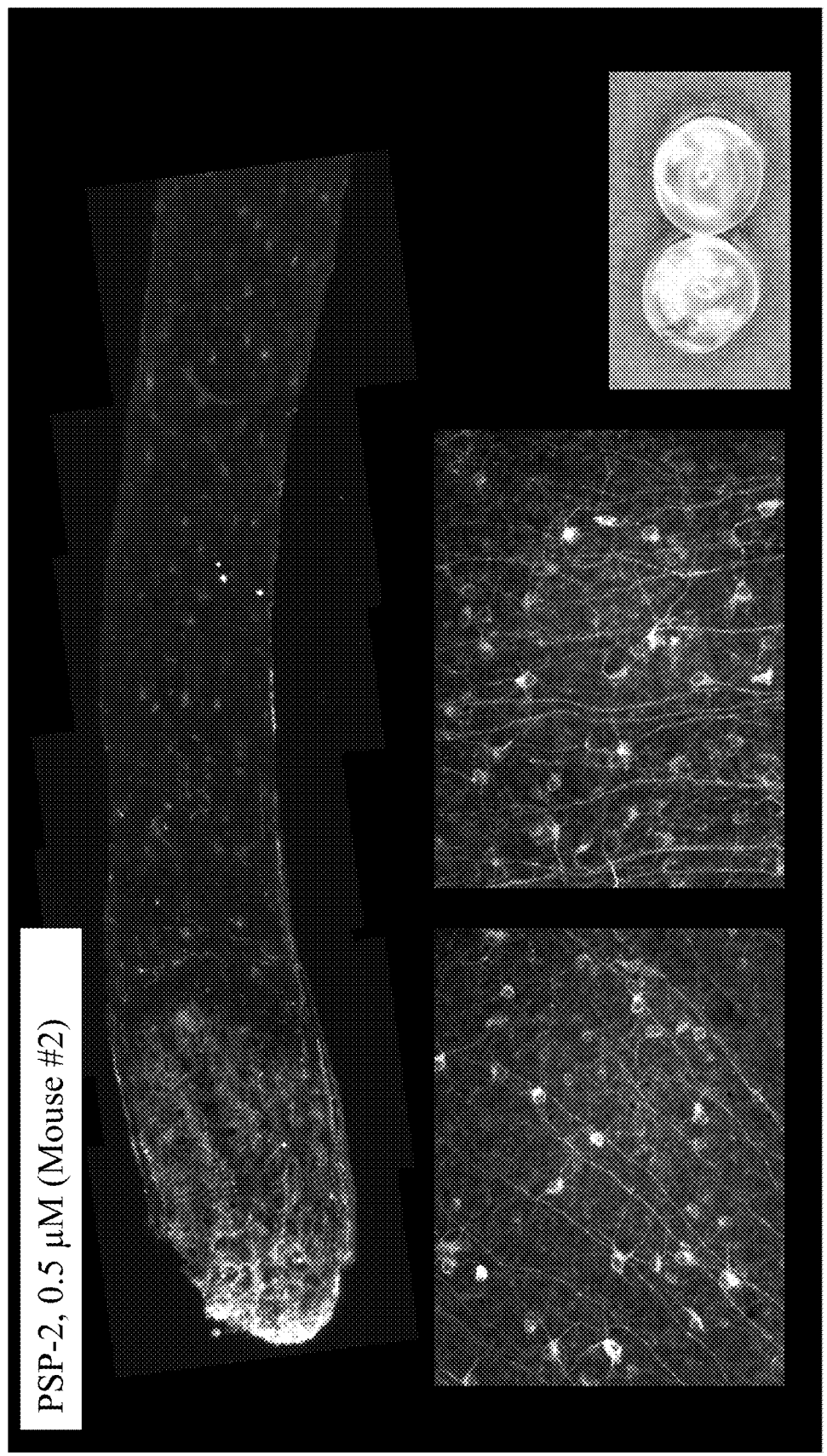
Figure 7H:
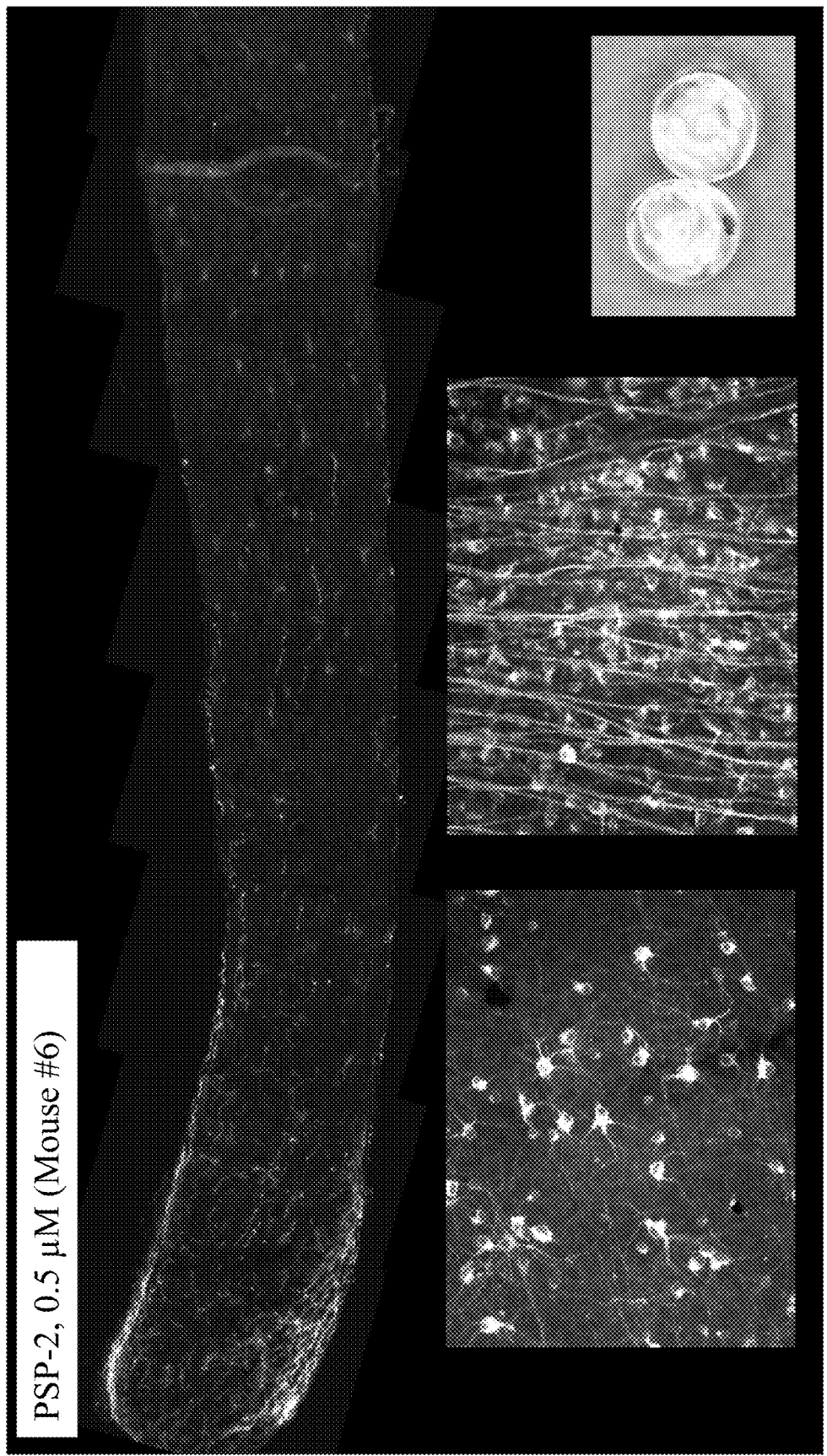
Figure 7I:
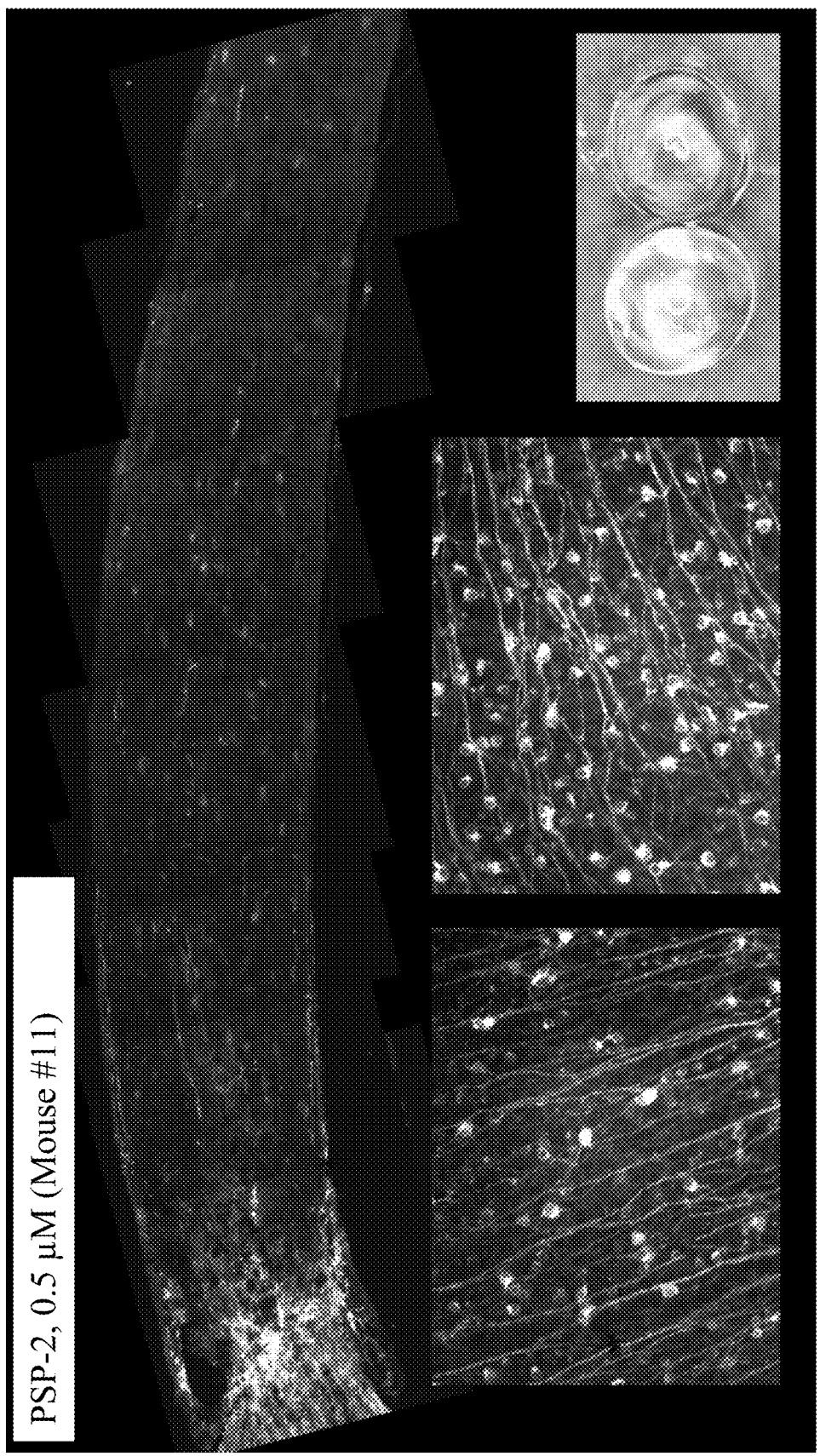
Figure 7J:
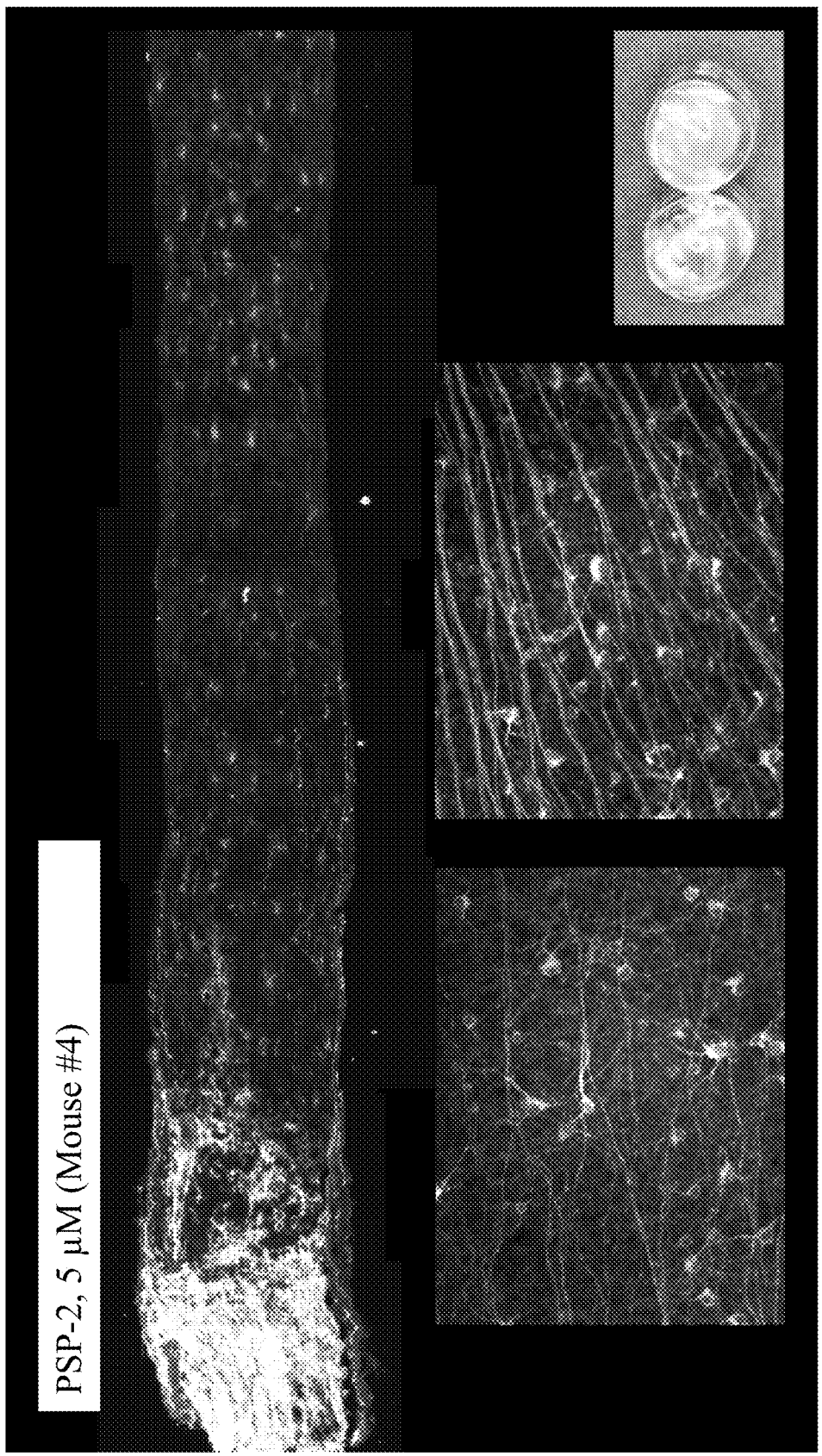
Figure 7K:
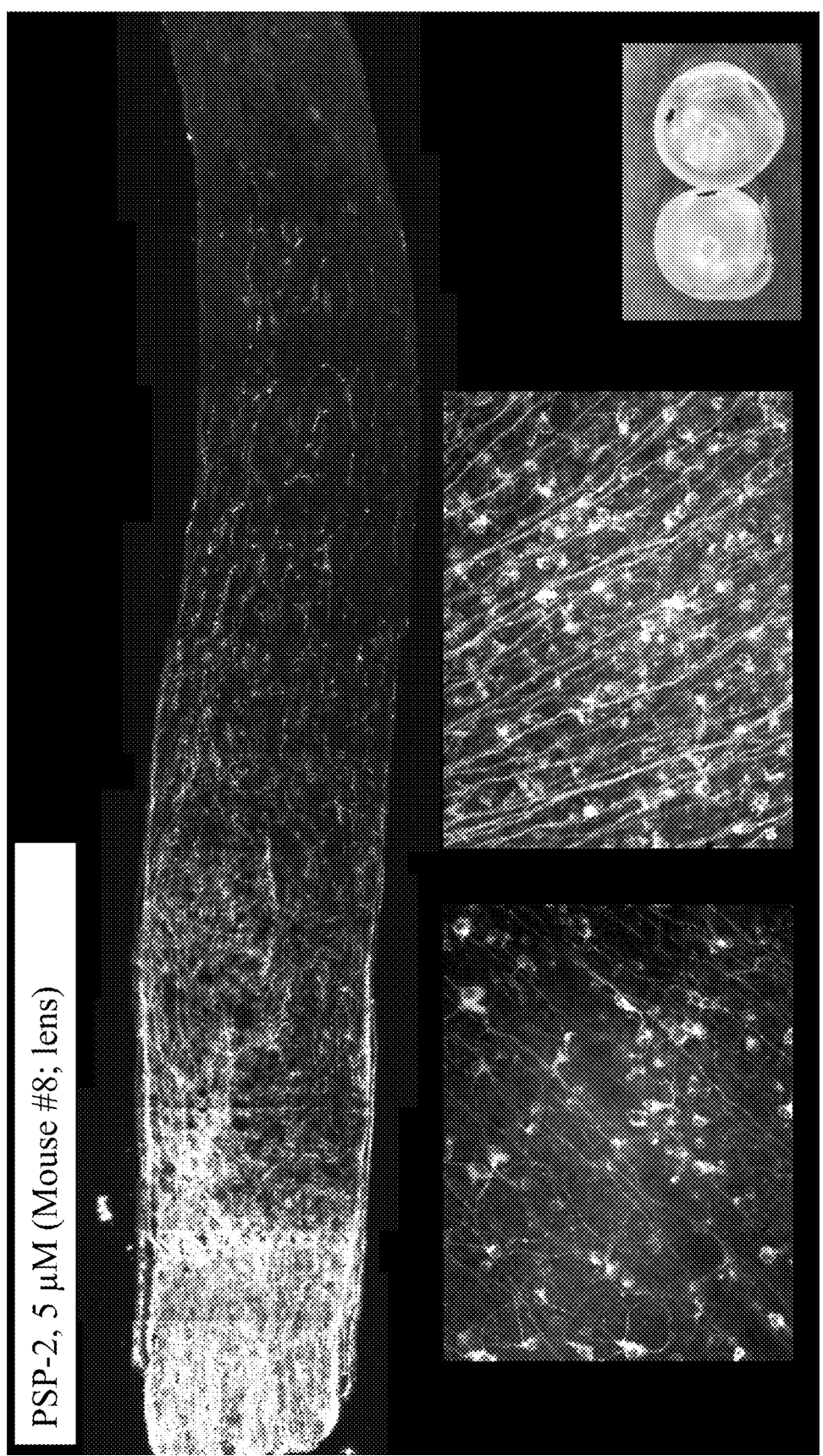
Figure 7L:
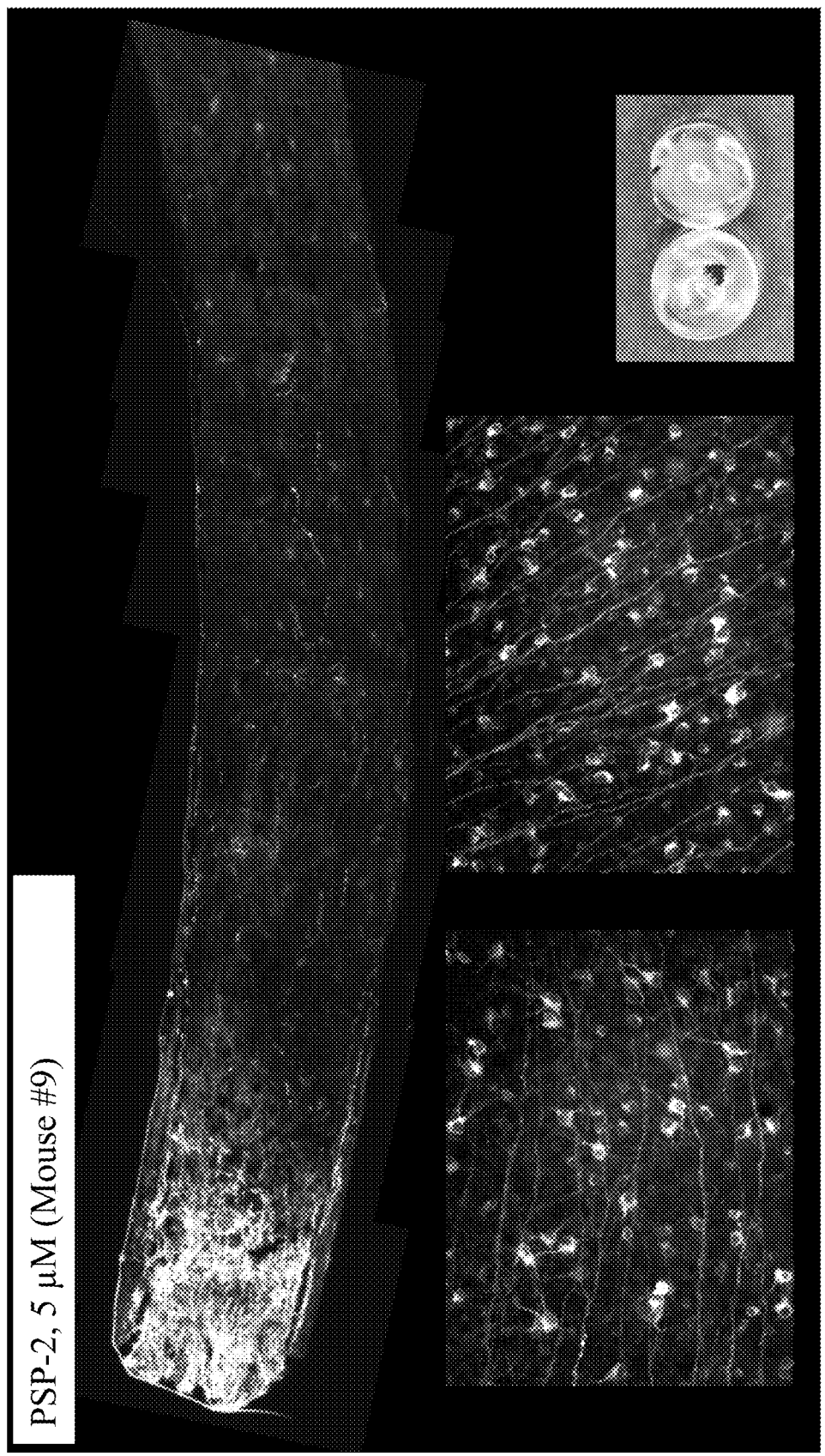
Figure 7M:
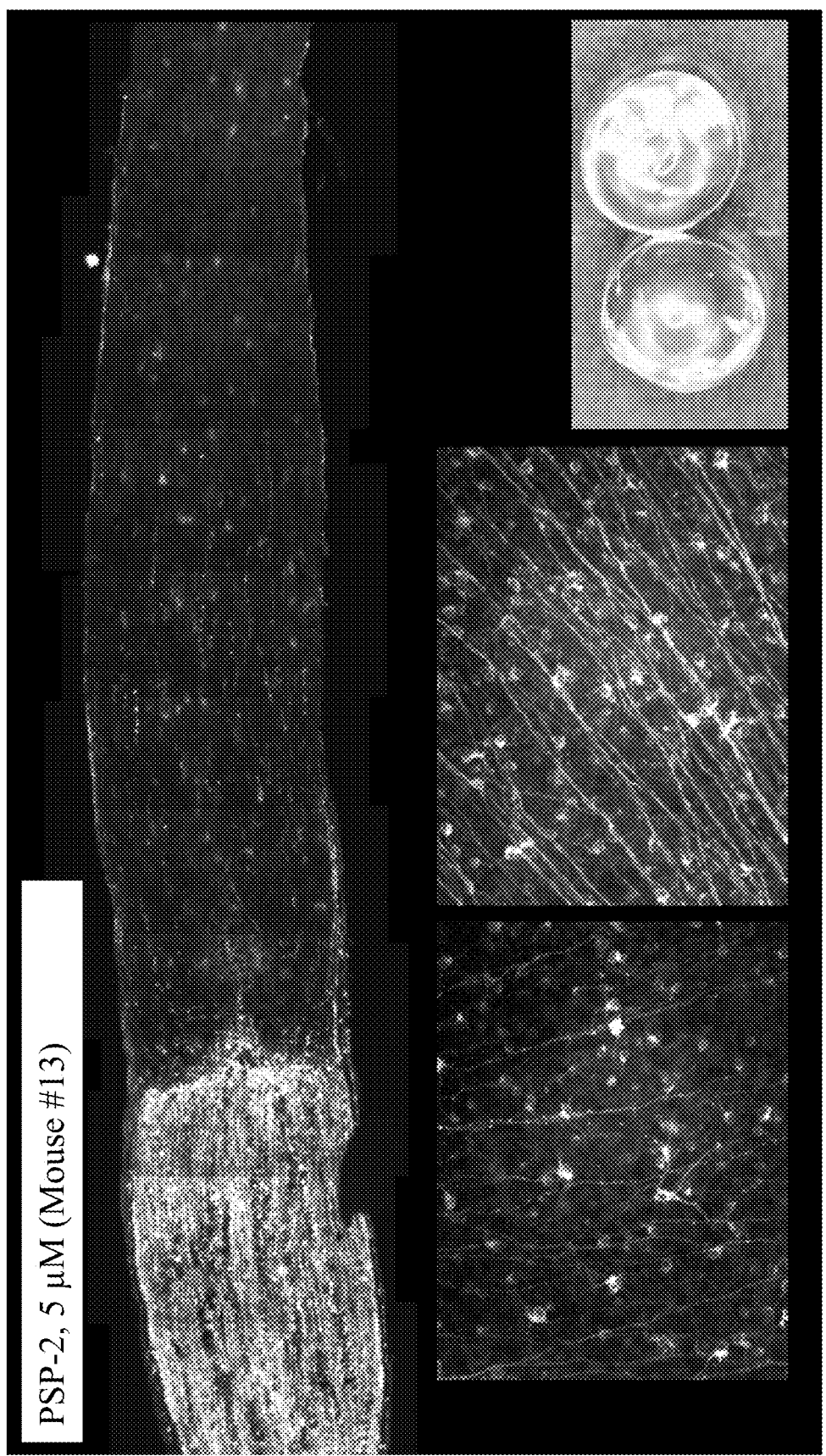
Figure 7N:
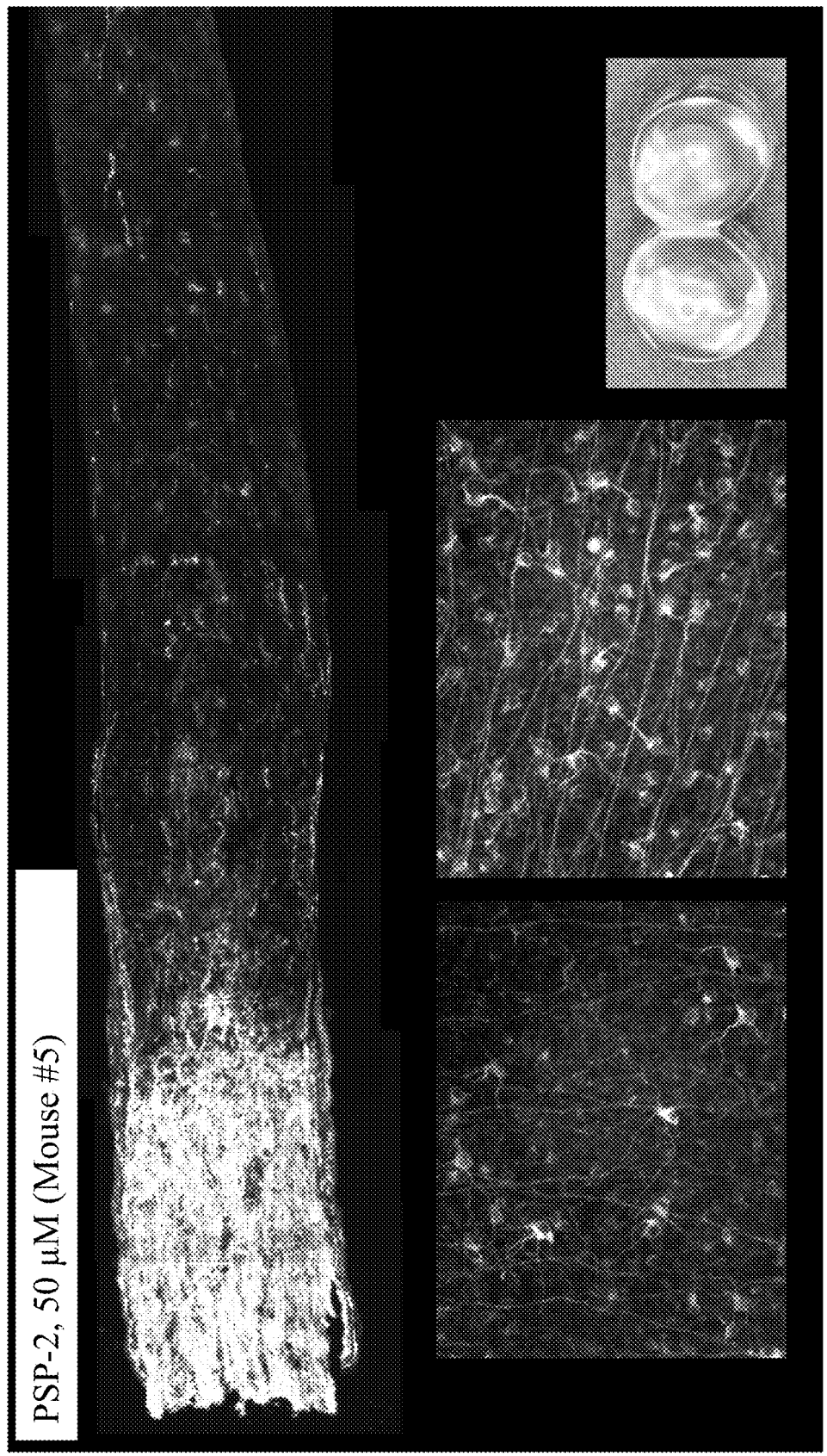
Figure 7O:
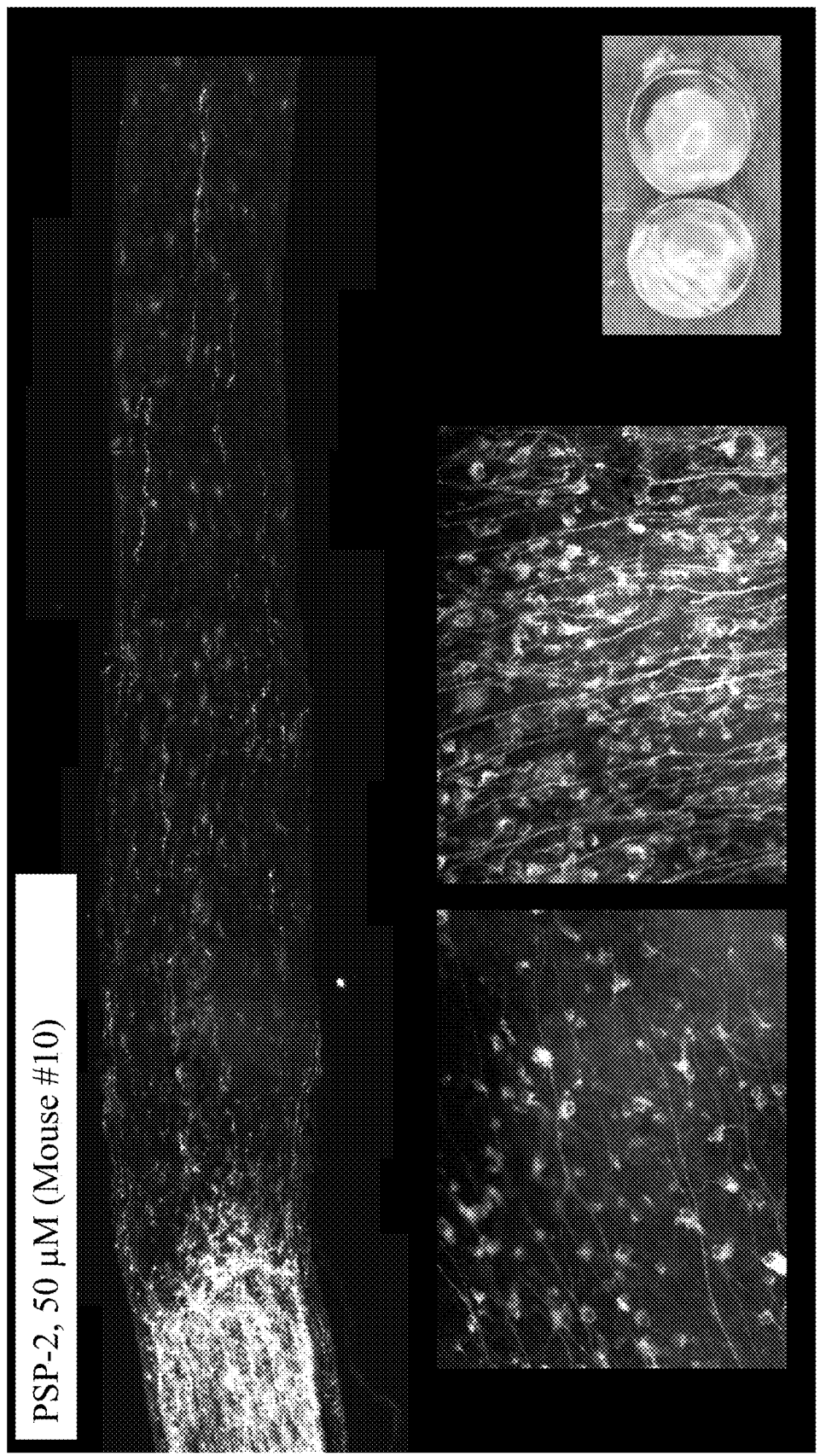
Figure 7P:
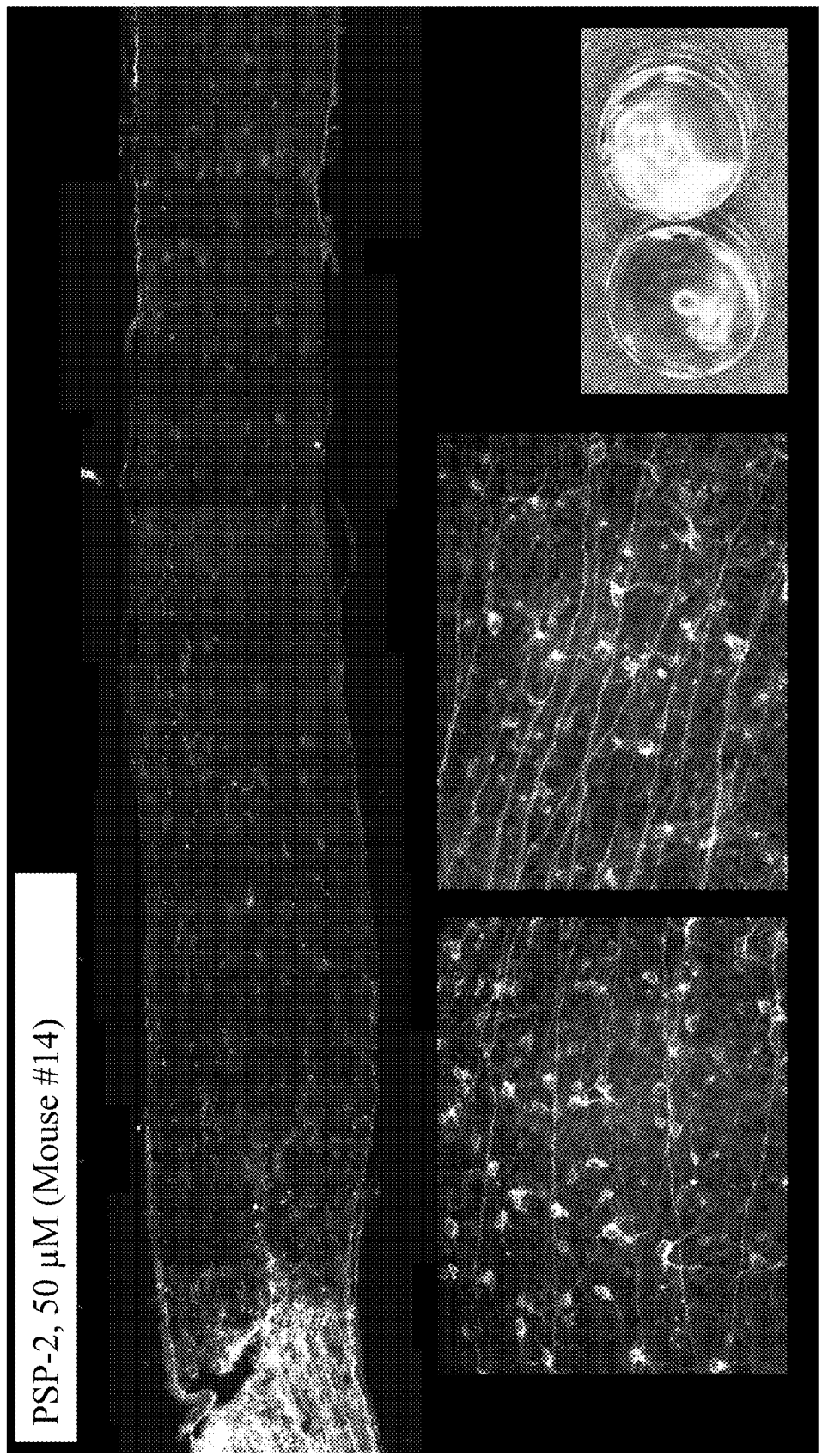
Figure 7Q:
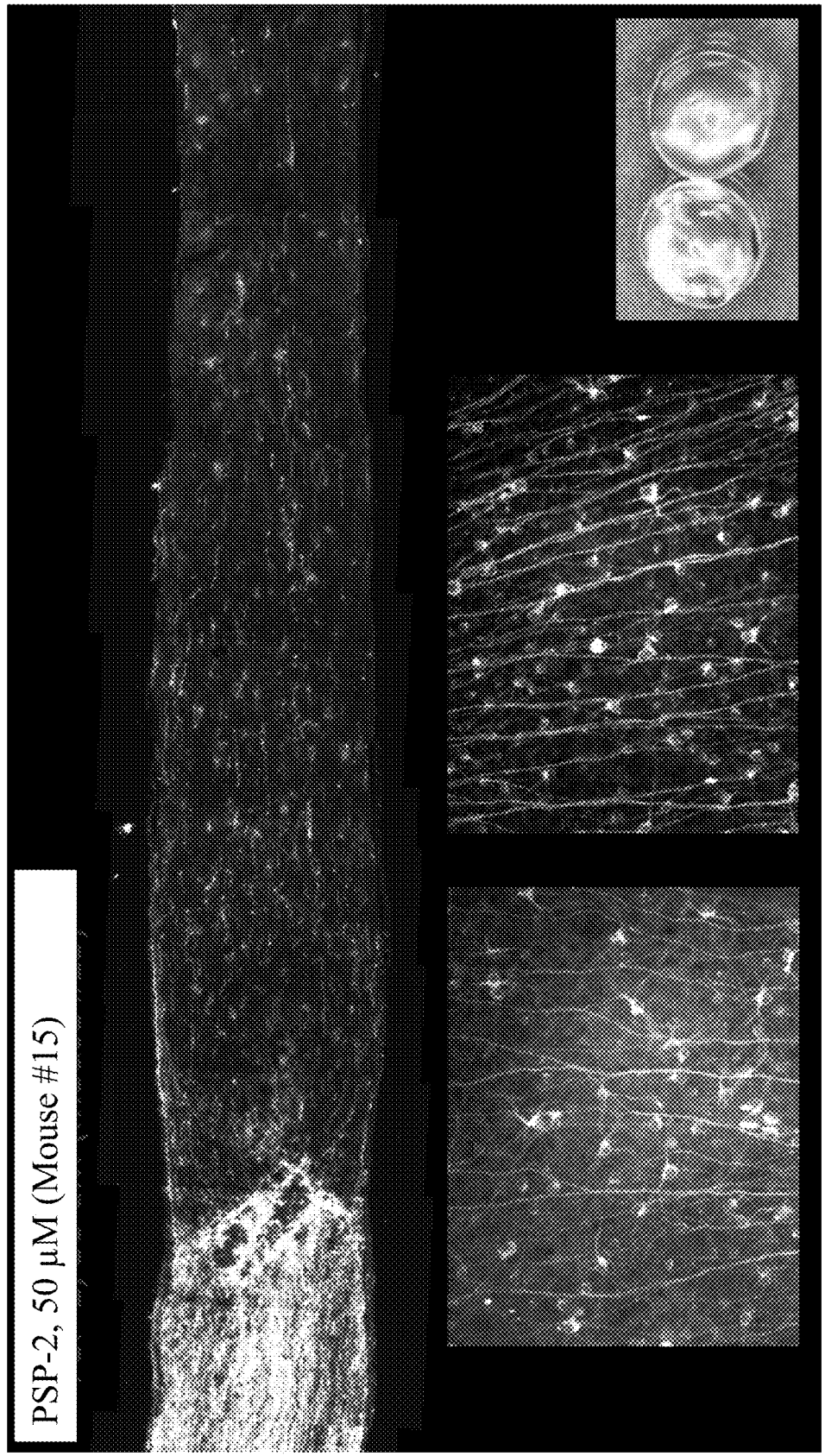
Figure 8:
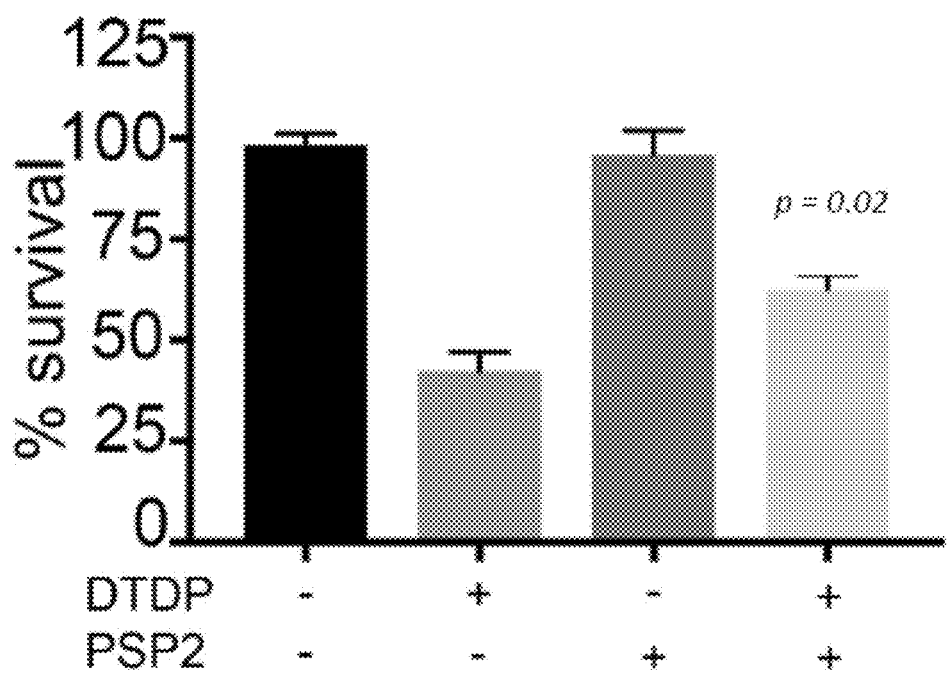
FIG. 8 is a bar plot showing that DTDP (dithiodipyridine) toxicity in astrocyte-rich primary cortical neurons was reversed with PSP-2 (3 µM). DTDP is an agent oxidizing metallothioneins. Oxidation of metallothioneins leads to liberation of metals (zinc and copper) and cell death.
Figure 9:
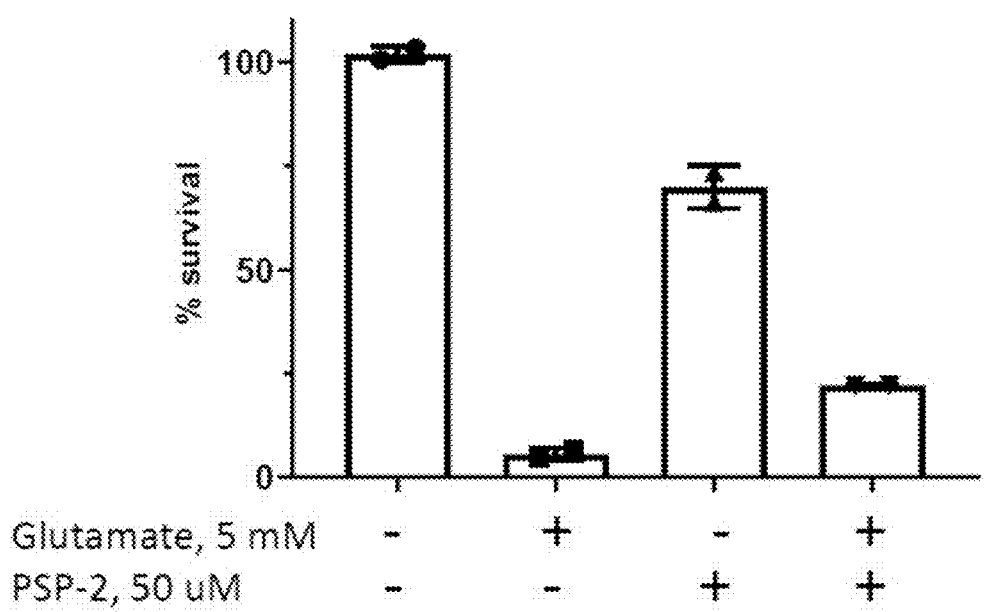
FIG. 9 is a bar plot showing that glutamate toxicity in HT22 cell culture was partially alleviated with PSP-2 (50 µM). Glutamate toxicity is a model of ferroptotic cell death. Glutamate toxicity and ferroptosis are likely involved in retinal ganglion cell (RGC) death post-optic nerve crush (ONC).

Example 3: PSP-2 Chelates Metal, Improves Axon Regeneration in a Dose-Dependent Manner, and Protects Against Metal Toxicity FIGS. 6A and 6B demonstrate that PSP-2 chelated retinal metal. PSP-2 (50 µM) reduced metal autometallography (AMG) signal in the retina, day 1 post optic nerve crush (ONC). FIGS. 7A to 7Q demonstrate that PSP-2 improved axon regeneration in a dose-dependent manner. FIG. 8 shows results from an in vitro study of PSP-2 demonstrating that PSP-2 protected against dithiodipyridine-(DTDP) induced cell death. DTDP toxicity in astrocyte-rich primary cortical neurons was reversed with PSP-2 (3 FIG. 9 shows results from an in vitro study of PSP-2 demonstrating that PSP-2 protected against glutamate-induced cell death. Glutamate toxicity in HT22 cell culture was partially alleviated with PSP-2 (50

Materials and Methods

Experiments were performed in 8 to 9-week-old 129S1/SvImJ male mice (Jackson Laboratory, Bar Harbor, Me.). Mice were anesthetized prior to ONC surgery with ketamine and xylazine. The ONC surgery and euthanization of mice were performed as previously described in U.S. Publication No. 2014/079741, the contents of which are hereby incorporated by reference in their entirety. Briefly, a conjunctival incision was made over the dorsal aspect of one eye, which was then gently rotated downward in the orbit. The orbital muscles were slightly separated to expose the optic nerve at its exit from the globe, which was then crushed for 5 seconds with jewelers' forceps (Dumont number 5) near the back of the eye (within 0.5 mm). ONC was performed unilaterally for all autometallography experiments and bilaterally for all regeneration experiments. Treatments were administered unilaterally for all autometallography experiments and bilaterally for all regeneration experiments. Post-ONC treatments were administered by intraocular injection immediately after ONC surgery. Mice were sacrificed with an overdose of anesthesia. Tissue samples were snap-frozen for all autometallography experiments. Mice were perfused with saline followed by 4% paraformaldehyde (PFA) and the tissue samples were post-fixed in PFA for regeneration experiments. Regenerating axons were stained using a primary anti-GAP-43 antibody followed by a fluorescently labeled secondary antibody. Retinal ganglion cells that survived were stained using a primary anti-βIII-tubulin antibody followed by a fluorescently labeled secondary antibody.

Axon growth was determined by counting GAP-43-positive axons extending 0.5 and 1 mm from the crush site. The cross-sectional width of the nerve was measured at the 0.5 and 1 mm points. The number of axons per millimeter of nerve width was calculated and then averaged for the number of sections analyzed. The estimated number of axons per nerve was then calculated. Retinal ganglion cell survival was measured as the number of βIII-tubulin positive cells per mm$^2$.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of treating a subject having a neuronal injury, the method comprising administering to the subject a composition comprising a phosphine sulfide-stabilized phosphine and a pharmaceutically acceptable carrier excipient, wherein the phosphine sulfide-stabilized phosphine is PSP-1 having the structure

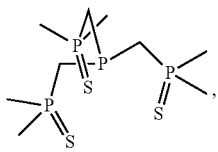

PSP-1

PSP-2 having the structure

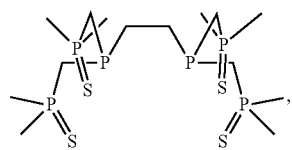

PSP-2 phenPS having the structure

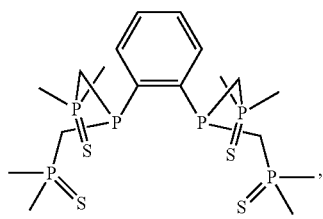

phenPS or naphPS having the structure

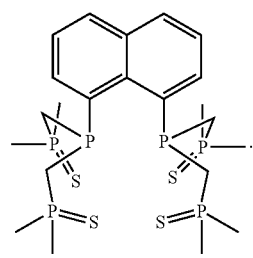

naphPS

2. The method of claim 1, wherein the phosphine sulfide-stabilized phosphine is PSP-2.

3. The method of claim 1, wherein the composition comprises an amount of a phosphine sulfide-stabilized phosphine sufficient to increase axon outgrowth subsequent to nerve injury relative to the amount of axon outgrowth detected in a corresponding control cell.

* * * * *